(12) United States Patent
Han et al.

(10) Patent No.: US 9,169,200 B2
(45) Date of Patent: Oct. 27, 2015

(54) POLYMER SUPPORTED REAGENTS AND METHODS OR REDUCING AROMATIC NITRO COMPOUNDS BY USING THE SAME

(75) Inventors: Yang-Kyoo Han, Seoul (KR); Jin Cho, Pyeongtaek-si (KR); Sang-Mi Lee, Seoul (KR); Seung-Hoon Shin, Seoul (KR)

(73) Assignees: LG CHEM, LTD., Seoul (KR); IUCF-HYU (INDUSTRY-UNIVERSITY COOPERATION FOUNDATION HANYANG UNIVERSITY), Seoul (KR)

(*) Notice: Subject to any disclaimer, the term of this patent is extended or adjusted under 35 U.S.C. 154(b) by 0 days.

(21) Appl. No.: 13/992,607

(22) PCT Filed: Mar. 16, 2012

(86) PCT No.: PCT/KR2012/001928
§ 371 (c)(1),
(2), (4) Date: Jun. 7, 2013

(87) PCT Pub. No.: WO2012/128515
PCT Pub. Date: Sep. 27, 2012

(65) Prior Publication Data
US 2013/0253083 A1    Sep. 26, 2013

(30) Foreign Application Priority Data
Mar. 18, 2011    (KR) .................... 10-2011-0024524

(51) Int. Cl.
| | | |
|---|---|---|
| *C08F 20/54* | (2006.01) | |
| *C08F 20/56* | (2006.01) | |
| *C08F 12/08* | (2006.01) | |
| *C07C 245/00* | (2006.01) | |
| *B01J 27/26* | (2006.01) | |
| *C07C 291/08* | (2006.01) | |
| *C08F 212/08* | (2006.01) | |
| *C07C 201/04* | (2006.01) | |
| *C07C 213/02* | (2006.01) | |
| *C07C 245/08* | (2006.01) | |
| *C08F 220/56* | (2006.01) | |
| *C07C 207/02* | (2006.01) | |
| *C07C 209/36* | (2006.01) | |
| *C07C 209/38* | (2006.01) | |
| *C07C 209/40* | (2006.01) | |
| *B01J 31/06* | (2006.01) | |

(52) U.S. Cl.
CPC ............ *C07C 291/08* (2013.01); *B01J 31/06* (2013.01); *C07C 201/04* (2013.01); *C07C 207/02* (2013.01); *C07C 209/36* (2013.01); *C07C 209/38* (2013.01); *C07C 209/40* (2013.01); *C07C 213/02* (2013.01); *C07C 245/08* (2013.01); *C08F 20/54* (2013.01); *C08F 212/08* (2013.01); *C08F 220/56* (2013.01); *B01J 2231/641* (2013.01)

(58) Field of Classification Search
CPC .......... C08F 20/54; C08F 20/56; C08F 12/08; C07C 245/00; B01J 27/26
USPC ................ 521/88, 147, 95, 98; 534/572, 585; 564/416; 568/949
See application file for complete search history.

(56) References Cited

U.S. PATENT DOCUMENTS 6,960,298 B2 * 11/2005 Krotz et al. .............. 210/500.35
2003/0146145 A1    8/2003 Krotz et al.

FOREIGN PATENT DOCUMENTS

| | | |
|---|---|---|
| CN | 103189134 A | 7/2013 |
| CN | 103189135 A | 7/2013 |
| CN | 103237822 A | 8/2013 |
| JP | 2002-536292 A | 10/2002 |
| JP | 2008-114164 A | 5/2008 |
| KR | 10-2003-0049208 A | 6/2003 |
| KR | 10-0464846 | 1/2005 |
| KR | 10-2005-0056288 A | 6/2005 |
| KR | 10-2012-0046004 A | 5/2012 |
| KR | 10-2012-0046005 A | 5/2012 |
| WO | WO 2006/0030414 | * 1/2006 |

OTHER PUBLICATIONS

"Preparation of Porous Crosslinked Copolymer Patricles from DPAA and Vinyl Monomers by a Suspension Polymerization and Their Applications as Polymeric Reagents for Hydrogenations" ; Cho, et al.; In Abstract for the Annual Meeting of the Polymer Society of Korea; 2008.
Highly Selective Reduction of Nitrobenzene Derivatives to Azoxybenzene Compounds Using a New Porous Polymer Reagent; Lee , et al. In Abstract of the Annual Meeting of the Polymer Society of Korea; 2010.
"Preparation of Porous Crosslinked Copolymer Patricles from DPAA and Vinyl Monomers by a Suspension Polymerization and Their Applications as Polymeric Reagents for Hydrogenations"; Cho, et al.; In Abstract for the Annual Meeting of the Polymer Society of Korea; 2008.
"The Reduction of Nitrobenzene Derivatives Using a New Polymer Reagent"; Lee, et al. In Abstract of the Annual Meeting of the Polymer Society of Korea; 2009.

(Continued)

*Primary Examiner* — Nathan M Nutter
(74) *Attorney, Agent, or Firm* — Dentons US LLC

(57) ABSTRACT

The present invention relates to a polymer supported reagent comprising a novel crosslinked mesoporous polymer, enabling a simple and easy production of an azoxy compound or an azo compound from an aromatic nitro compound, and a method of selectively reducing an aromatic nitro compound by using the same. The polymer supported reagent comprises a certain acrylamide mesoporous crosslinked polymer.

19 Claims, 9 Drawing Sheets

(56) References Cited

OTHER PUBLICATIONS

Highly Selective Reduction of Nitrobenzene Derivatives to Azaxybenzene Compounds Using a New Porous Polymer Reagent; Lee, et al. In Abstract of the Annual Meeting of the Polymer Society of Korea; 2010.

"Highly Selective Reduction of Nitrobenzene Derivatives Using a New Microporous Polymer Reagent"; Lee, et al.; In Abstract of the Annual Meeting of the Polymer Society of Korea; 2010.

\* cited by examiner

POLYMER SUPPORTED REAGENTS AND METHODS OR REDUCING AROMATIC NITRO COMPOUNDS BY USING THE SAME

This application is a National Stage Entry of International Application No. PCT/KR2012/001928 filed Mar. 16, 2012, and claims the benefit of Korean Application No. 10-2011-0024524 filed on Mar. 18, 2011 all of which are hereby incorporated by reference in their entirety for all purposes as if fully set forth herein.

TECHNICAL FIELD

The present invention relates to novel polymer supported reagents and methods of selectively reducing an aromatic nitro compound by using the same. More specifically, the present invention is directed to polymer supported reagents enabling a simple and easy production of azoxy or azo compounds from aromatic nitro compounds, and methods of selectively reducing aromatic nitro compounds by using the same.

BACKGROUND OF THE ART

Polymer-supported reagents are a crosslinked polymer with a functional group capable of triggering a chemical reaction as bonded to the polymer chains. A crosslinked polystyrene is widely used for such polymer supported reagent since a functional group may be more easily introduced thereto. For example, there have been known in the art the polymer supported reagents such as ion exchange resins having a benzene ring with an anionic or cationic group attached thereto or a crosslinked polystyrene with a protective group for a protein synthesis bonded thereto, also well-known as a polymer supported reagent for Merrifield synthesis. Besides, different types of polystyrene supported reagents find their applications in synthesis of various organic compounds and in purification reactions.

The polymer supported reagents are advantageous in that they are easy to separate after a reaction, and can be reused, as well. Moreover, they hardly have toxicity or odor in comparison with a low molecular weight reagent. However, they are very expensive and show a low level of reactivity since the functional group introduced to the polymer chain has a poor mobility. Recently, however, vigorous researches on polymer supported reagents of a novel structure are under way in order to address aforementioned problems. Depending on their intended use, the polymer supported reagents may be utilized as ion exchange resins, substrates for synthesis of proteins or other specific organic compounds, catalysts, agents for separating and transferring a special reagent, and the like. Among them, studies have been made most intensively on the use for the organic synthesis substrates and catalysts.

It has been known that aromatic nitro compounds such as nitrobenzene derivatives may be easily reduced to an aniline compound by means of various hydrogenation catalysts. Metallic reducing agents such as Ranny Ni, $PtO_2$, Zn/HCl, $Al/NH_4Cl/MeOH$, or $NaBH_4/BiCl_3$ have been commonly known as the catalyst for such reduction reaction. These catalysts are, however, very expensive, entails using an organic solvent, are sensitive to moisture, and sometimes require a reaction to be carried out at a high pressure.

Catalysts such as $Zn/NH_4Cl$ or an ionic liquid have been recently developed in an effort to remedy these shortcomings. By using these catalysts, aromatic nitro compounds such as nitrobenzene may be reduced in water to produce aniline compounds in high yield up to 80%. However, such a reduction reaction alone may not lead to the production of aromatic azoxy-, azo-, or hydrazo-compounds such as expensive azoxybenzene, azobenzene, or hydrazobenzene, which are widely used for a dye, a pigment, an analytic reagent, a reducing agent, a stabilizer, an intermediate for a medicine and in an organic synthesis, or a polymerization inhibitor.

It was previously known that these compounds may be obtained by subjecting an aniline compound as a starting material to an oxidation in the presence of an expensive special catalyst such as sodium tungstate/hydrogen peroxide, magnesium sulfate/aluminum oxide or $Au/TiO_2$ and then subjecting the intermediate product thus obtained, e.g., phenyl hydroxy amine and nitroso benzene to a coupling reaction therebetween. In this method, as a starting material, the aromatic nitro compound such as nitrobenzene is reduced to provide an aniline compound, which is then used for synthesizing an azoxy compound, an azo compound, or a hydrazo compound via the aforementioned coupling reaction. However, the reaction using such expensive catalyst and the multi-stage reduction reaction make the production process extremely complex and complicated and their yield is not really high, as well. Moreover, a mixture of different compounds is disadvantageously produced therefrom.

Therefore, there has been a need for a method of easily producing azoxy-, azo- or hydrazo compounds from the aromatic nitro compound through a more simple reaction process.

DETAILED DESCRIPTION OF THE INVENTION

Technical Objectives

Thus, the present invention is to provide a novel polymer-supported reagent allowing a simple and easy production of azo compounds and the like from an aromatic nitro compound.

Further, the present invention is to provide a method of reducing an aromatic nitro compound by using the polymer supported reagent, through which one may easily and simply obtain azoxy compounds and the like from the aromatic nitro compound in high yield.

Technical Solutions

The present invention provides a polymer supported reagent comprising an acrylamide mesoporous crosslinked polymer comprising at least one repeating unit of Chemical Formula 1:

[Chemical Formula 1]

$$-\!\!\left[CH_2-\underset{\underset{O=C-NH-R'}{|}}{\overset{\overset{R}{|}}{C}}\right]_{\!n}\!\!-$$

in Chemical Formula 1, n is an integer of 15 to 1800,
R is hydrogen or methyl,
R' is X,

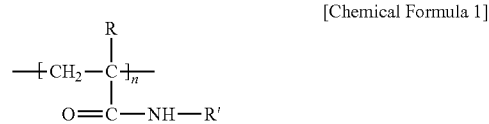

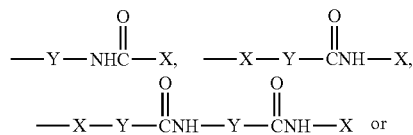

-continued

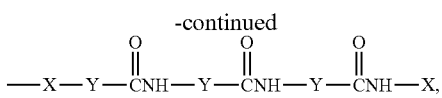

X is —Z—R″,
Y is an alkylene of C1 to C10,
Z is an arylene of C6 to C20, and
R″ is a linear or branched hydrocarbon of C10 to C20, or a linear or branched perfluorohydrocarbon of C10 to C20.

In addition, the present invention provides a method of producing the polymer supported reagent, which comprises the step of subjecting a monomer composition including an acrylamide monomer of Chemical Formula 2 to a suspension polymerization in the presence of a crosslinker and a radical initiator:

[Chemical Formula 2]

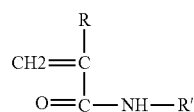

In Chemical Formula 2, R and R' are the same as defined in Chemical Formula 1.

Further, the present invention provides a method of reducing an aromatic nitro compound, which comprises the step of subjecting an aromatic nitro compound to a reduction reaction in the presence of the polymer supported reagent and a reducing catalyst.

Now, the polymer supported reagents according to specific embodiments of the present invention and the production method thereof, and the method of reducing an aromatic nitro compound by using the same will be explained in detail.

According to an embodiment of the present invention is provided a polymer supported reagent comprising an acrylamide mesoporous crosslinked polymer having at least one repeating unit of Chemical Formula 1:

[Chemical Formula 1]

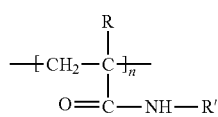

in Chemical Formula 1, n is an integer of 15 to 1800,
R is hydrogen or methyl,
R' is X,

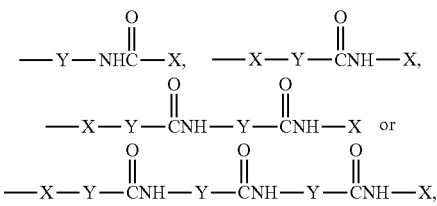

X is —Z—R″,
Y is an alkylene of C1 to C10,
Z is an arylene of C6 to C20, and
R″ is a linear or branched hydrocarbon of C10 to C20, or a linear or branched perfluorohydrocarbon of C10 to C20.

The present inventors have discovered the followings to reach the present invention: using a polymer supported reagent including a certain type of acrylamide mesoporous crosslinked polymers makes it possible to prepare an aromatic azoxy-, azo-, or hydrazo compound, for which the prior arts could not help conducting a very complex and complicated reduction reaction of many steps, from an aromatic nitro compound through a very simple and easy reducing process.

As used herein, the term "polymer supported reagent" refers to any polymeric substances, the polymer chain of which includes a certain functional group bonded thereto to facilitate a particular type of a chemical reaction, or to selectively trigger or promote only a particular type of a chemical reaction. Examples of the chemical reaction allowing the use of such "polymer supported reagent" include a reduction reaction such as a certain reduction reaction of an aromatic nitro compound, and other than that, mentions may be made of various chemical reactions. In addition, the "polymer supported reagent" may be used alone or in combination with a catalyst, and this term may collectively denotes any polymeric substance other than catalysts or reactants, which is used for facilitating or selectively triggering or promoting the chemical reaction.

In an embodiment, using the polymeric supported reagent enables one to produce the azoxy compounds and the like more easily in high yield, and this may results from mesoporosity having regularity present in a certain acrylamide mesoporous crosslinked polymer. Such crosslinked polymers and the polymer-supported reagent comprising the same may be prepared by carrying out a specially designed suspension polymerization with a certain type of an acrylamide monomer (i.e., the monomer of Chemical Formula 2, the rest are the same as mentioned above), and they may have mesoporosity comprising many meso-sized pores without any additional chemical treatment due to the reasons as explained hereinbelow.

The acrylamide monomer being used in the production of such crosslinked polymers has a chemical structure with a non-polar aliphatic hydrocarbon (having at least 10 carbon atoms) capable of being self-assembled, an arylene group having interaction between π-π orbitals, and an amide group causing a intra- or inter-molecular hydrogen bonding. The self-assembling behavior of the aliphatic long-chain hydrocarbons, the π-π interaction of the arylene groups, and the intramolecular hydrogen bonding between the amide groups allow the monomer to form a regular, three-dimensional, monoclinic crystal structure in a solid state.

Therefore, if the polymerization reaction occurs with the monomer molecules being well-oriented, each monomer molecule in the polymer chain may be orderly arranged. More specifically, the well oriented monomer molecules are linked with each other through the polymerization reaction to form one polymer chain (e.g., one building block of polymer), and such building blocks of polymer may gather to form a orderly arranged polymer. Therefore, such polymer has the building blocks of the polymer orderly arranged therein so that the acrylamide crosslinked polymer may comprise many of uniformly sized mesopores, for example, having a diameter of about 2.0 to 10.0 nm without any further treatment after polymerization.

As such, the crosslinked polymer shows mesoporosity comprising many uniformly sized mesopores and thus, the polymer supported reagent based on such crosslinked polymer may be used in a reduction reaction of an aromatic nitro compound, allowing a selective production of the aromatic azoxy compound. Without being bound by any theory, technological reasons for enabling such selective production are presumed to be as follows.

Under the Arrhenius reaction kinetics, the reaction rate constant, k is proportionate to the number of effective collisions, A, and is inversely proportionate to an exponential function of the activation energy, Ea. That is, the following relation may be fulfilled: $k=Ae^{-(Ea/RT)}$ wherein R is the universal gas constant, T is a reaction temperature (kelvin temperature: K). Further, in such relation, the number of effective collisions, A is dependent on the collision direction between the reactants and the molecular orientation. Accordingly, as the number of effective collision increases, the activation energy decreases, and the reaction temperature is getting higher, the yield of the product may increase.

When the polymer supported reagent comprising such crosslinked polymer is used for the reduction reaction of the aromatic nitro compound, the aromatic ring of the aromatic nitro compound may be physically bonded beforehand among the numerous benzene groups existing in the chains of the crosslinked polymer. As a result, the aromatic rings of the aromatic nitro compound are stuck among the benzene groups present in the numerous mesopores of the polymer supported reagent comprising the crosslinked polymer and in such circumstances, selective reduction of the nitro group may occur. When the reduction reaction proceeds with using a reducing catalyst under the aforementioned condition, the number of the effective collisions against the nitro group of the aromatic nitro compound is expected to increase, allowing the reduction reaction to occur efficiently and selectively.

In other words, as the aromatic ring of the reactants (e.g., the aromatic nitro compound) undergoes a selective reduction reaction for the nitro group as fixed in the mesopores of the polymer supported reagent, the nitro group is exposed to the surface of the polymer supported reagent, and this makes the reduction reaction easier to occur. Moreover, unstable intermediate compounds such as a nitroso compound or a hydroxylamine compound first generated by the reduction reaction may be kept in a stabilized state by the fixing effect of the aromatic rings, and the intermediate products may undergo a coupling reaction very efficiently because of the orientation effect wherein they are placed very close to each other. Accordingly, the aromatic azoxy compounds and the like may be obtained more easily. The reaction mechanism can be explained by the following Reaction Scheme 1:

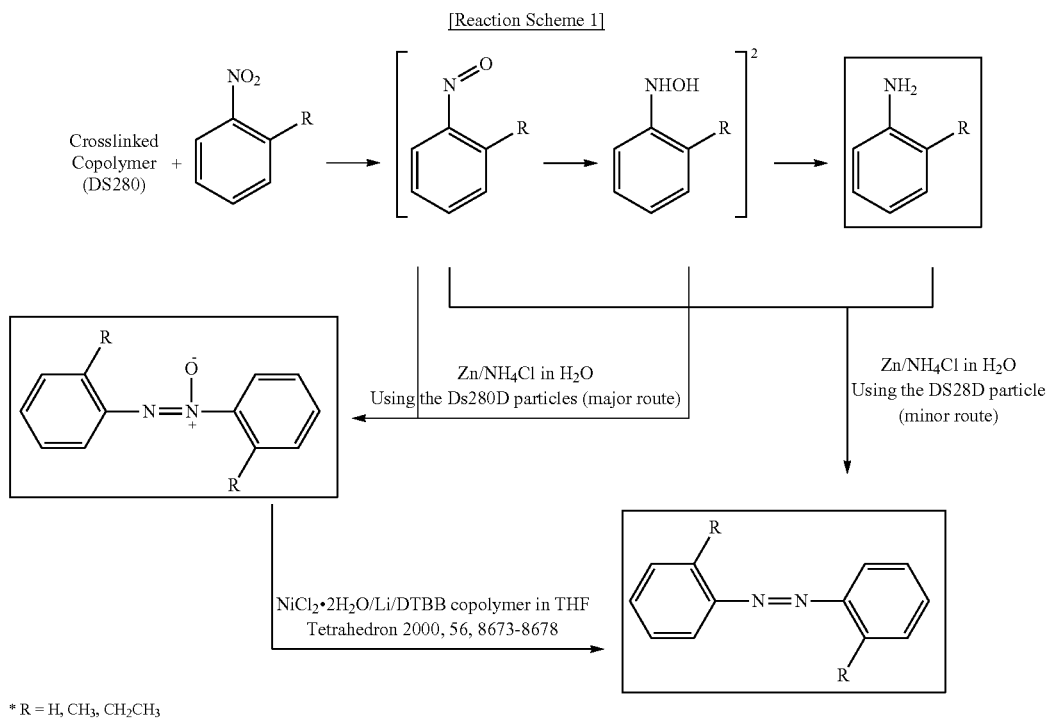

Referring to Reaction Scheme 1, the reduction reaction being conducted with an aromatic nitro compound such as nitrobenzene may form as an intermediate product a nitroso compound such as nitroso benzene or a hydroxylamine compound such as phenyl hydroxylamine, which have a typically unstable chemical structure. For that reason, the intermediate product in the reduction method according to the prior arts failed to be stabilized and ended up being converted to an aniline compound, and thus an additional coupling reaction entailing the use of an expensive catalyst had to be conducted with such aniline compounds so as to obtain the aromatic azoxy- or azo-compounds. With using the polymer supported reagent of an embodiment, however, the fixation effect of the aromatic rings resulting from the aforementioned mesoporosity may stabilize the intermediate product, and the coupling reaction may occur very efficiently due to the orientation effect wherein the intermediate products are located very close to each other. Therefore, using the polymer supported reagent can facilitate the production of the azoxy compounds and the like, from which one may obtain an aromatic azo compound very easily.

Based on such reasons, when the polymer supported reagent of an embodiment is applied to the reduction reaction of the aromatic nitro compound, the azoxy compound and the like may be produced through a simplified single reduction reaction in high yield. The results of the experiments conducted by the present inventors revealed that by using the polymer supported reagent of the embodiment in conjunction with a conventional reducing catalyst typically used in the reduction reaction of the aromatic nitro compound, the aromatic azoxy compound, which had been difficult to produce in prior arts, may be prepared through a single-stage reduction reaction with a very high yield of at least 70%.

Hereinafter, the polymer supported reagent comprising the crosslinked polymer and the production method thereof, and the reduction method by using the same will be explained more specifically.

In the acrylamide repeating unit of the crosslinked polymer contained in the polymer supported reagent, Z is an arylene group having 6 to 20 carbon atoms. More specifically, examples of the arylene group include o-phenylene

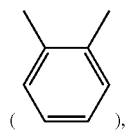

m-phenylene

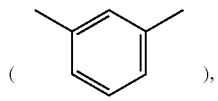

p-phenylene

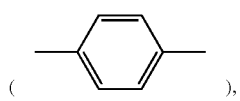

naphthalene

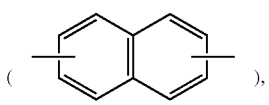

azobenzene

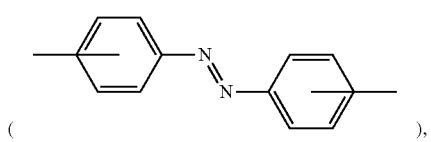

anthracene

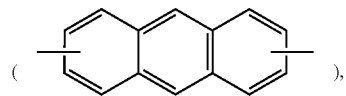

phenanthrene

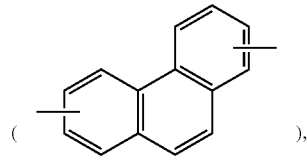

tetracene

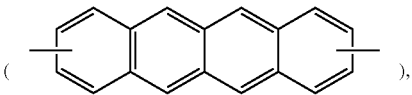

pyrene

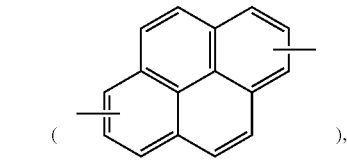

benzopyrene

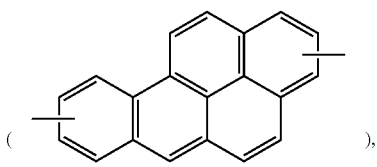

and the like, and other various arylene group may be utilized.

In addition, R" is a linear or branched hydrocarbon group substituted at the o-, m-, or p-position of the aromatic ring being included in Z, and the hydrocarbon has a long chain length of at least 10 carbon atoms, more specifically, 10 to 20 carbon atoms. In addition, the hydrocarbon group of R" may be substituted with fluorine and R" may be a linear or branched perfluorohydrocarbon of C10 to C20. As the repeating unit of Chemical Formula 1 and the monomer of Chemical Formula 2 have a long chain hydrocarbon and arylene groups, the mesoporosity of the crosslinked polymer may become more remarkable.

The crosslinked polymer can be a homopolymer consisting of one type of a repeating unit of Chemical Formula 1 or otherwise a copolymer comprising at least two types of such repeating units or further comprising one or more polymer repeating units selected from the group consisting of a styrene repeating unit and a vinyl repeating unit. The styrene repeating unit may be a repeating unit derived from styrene or a para-alkyl (or hydroxyl) styrene derivative. The vinyl repeating unit may be a repeating unit derived from n-alkyl(meth)acrylate or acrylonitrile.

In addition, the crosslinked polymer in the form of homopolymer or copolymer has to comprise the repeating unit of Chemical Formula 1 and optionally includes the styrene repeating unit. By way of an example, it may comprise these two types of repeating units in a mole ratio of about 10:0 to 1:9. More specifically, when the crosslinked polymer is a copolymer comprising the repeating unit of Chemical Formula 1 together with the styrene repeating unit, these repeating unit may be included at a mole ratio of about 9:1 to 1:9, or about 5:5 to 2:8. With the styrene repeating unit being included at a predetermined mole ratio, the polymer supported reagent as used in the reduction reaction of the aromatic nitro compound can stabilize a more amount of the aromatic nitro compound, thus further enhancing the productivity of the selective reduction reaction.

Moreover, the crosslinked polymer may comprise many mesopores having a diameter of about 2.0 to 10.0 nm or about 2.0 to 6.0 nm in a solid state. In this regard, the "diameter" of the pores may be defined as the length of the longest straight line among the lines connecting two different points on a circle, an oval, or a polygonal of the cross-section of each pore. As the polymers include plenty of uniform mesopores having a diameter within such range, the polymer supported reagent comprising the same may stabilize the aromatic nitro compound and the reduction intermediate product thereof (e.g., an aromatic nitroso compound or a hydroxylamine compound) more effectively, thereby enhancing the yield of the azoxy compound and the like.

In addition, the polymer supported reagent comprising the crosslinked polymer may have different shapes, but it can properly have a shape of a spherical particle, for example, a spherical particle shape having about 20 to 300 μm, or about 50 to 200 μm. As the polymer supported reagent has the spherical particle shape of a predetermined scale comprising many mesopores, it can be effectively brought into contact with the reactant such as the aromatic nitro compound and fix the same, and it may stabilize the reduction intermediate product, as well.

In the case of a crosslinked polymer comprising at least 50 mol % of the repeating unit of Chemical Formula 1, more specifically about 50 to 100 mol % of the main repeating units, when being subjected to a heat treatment at a temperature of at least about 200° C. but below its melting temperature, for example, at a temperature of about 220° C. to 240° C., it may have mesopores of a decreased diameter with increasing the temperature of heat treatment. For example, as the temperature of the heat treatment increases, the diameter of the mesopores may decrease by about 0.4 to 0.7 nm, more specifically, by about 0.5 to 0.6 nm.

The crosslinked polymer comprising the repeating unit of Chemical Formula 1 as a main repeating unit may have mesopores with an increased diameter as it has an increased length of the chemical structure of R' bonded to the amide (—CO—NH—) group being included in the repeating unit of Chemical Formula 1 or the aliphatic hydrocarbon bonded at its end, for example, an increased carbon number of the hydrocarbon or the perfluorohydrocarbon corresponding to R". For example, as the carbon number increases from 12 to 16, the diameter of the mesopores may increase by about 0.1 to 1.0 nm, more specifically by about 0.2 to 0.7 nm. As the chemical structure of Z being included in the R' has different aromatic structures from phenylene to naphthalene or anthracene, the diameter of the mesopores may increase.

The changes in the diameter of the mesopores are expected to result from the change in the three-dimensional structure of the mesopores of the crosslinked polymers caused by the heat treatment or the change in the chemical structure of R' or the carbon number of R" bonded at its end.

As such, in the crosslinked polymers and the polymer supported reagent comprising the repeating unit of Chemical Formula 1 as a main repeating unit, the size of the mesopores may be easily controlled by means of carrying out a heat treatment, changing the chemical structure introduced into the amide group of the repeating unit, or controlling the length of the hydrocarbon. The polymer supported reagent may be, therefore, made to have suitable mesopores depending on the types of the reaction and the reactants as applied. Accordingly, it can be preferably used as a polymer supported reagent for promoting a certain type of reactions among various chemical reactions including the reduction reaction of the aromatic nitro compound.

According to other embodiment of the present invention is provided a production method of the polymer supported reagent. The production method of the polymer supported reagent comprises the step of subjecting a monomer composition including an acrylamide monomer of Chemical Formula 2 to a suspension polymerization in the presence of a crosslinker and a radical initiator:

[Chemical Formula 2]

In Chemical Formula 2, R and R' are the same as defined in Chemical Formula 1.

As such, the acrylamide monomer having a certain structure of Chemical Formula 2 is polymerized in the presence of the crosslinker and the radical initiator to provide an acrylamide crosslinked polymer with the aforementioned mesoporosity and a polymer supported reagent including the same. Sufficient explanations as to the reasons why the crosslinked polymer and the polymer supported reagent as prepared therefrom would have the mesoporosity have already been presented in the above, and thus further explanation will now be omitted. To the conclusion, the aforementioned polymerization process alone makes it possible to prepare the crosslinked polymer and the polymer supported reagent with no further chemical treatment.

In the production method, the suspension polymerization step may comprise the steps of dissolving the crosslinker, the radical initiator, and the monomer composition in an oil-soluble organic solvent to form an oil-soluble solution; and dispersing the oil-soluble solution in water with a surfactant dissolved therein and initiating the polymerization. As such, in water of a continuous phase with a surfactant dissolved therein is dispersed the oil-soluble solution of a discontinuous phase comprising the monomer composition, the crosslinker, the radical initiator, and the oil-soluble organic solvent and then the polymerization can be conducted to produce a polymer supported reagent comprising the crosslinked polymers in the form of a spherical particle, for example, with a particle size of 20 to 300 μm. At this time, the size and the shape of the particles of the polymer supported reagent may be controlled by modifying factors such as the ratio between the oil-soluble solution and water, the types and the concentrations of the surfactant used as a dispersing agent, the speed of agitating the dispersion solution, and the like. Among these factors, the surfactant allows the size and shape of the particles of the polymer supported reagent to be uniformly maintained not only by maintaining uniformly the size of the oil-soluble solution comprising the monomer discontinuously dispersed in water of a continuous phase but also by safely dissipating an excessive amount of polymerization heat as generated in water. The polymer supported reagent with a controlled size and shape obtained in this manner may be effectively applied to more various reactions and reactants.

In the production method, one may also use any acrylamide monomer having a structure of Chemical formula 2 as a monomer. Specific examples of the monomer include N-(p-dodecyl)phenyl acrylamide (DOPAM), N-(p-tetradecyl)phenyl acrylamide, (TEPAM), N-(p-hexadecyl)phenyl acrylamide (HEPAM), N-(p-dodecyl)naphthyl acrylamide (DONAM), N-(p-tetradecyl)naphthyl acrylamide (TENAM), N-(p-hexadecyl)naphthyl acrylamide (HENAM), N-(p-dodecyl)azobenzenyl acrylamide, (DOAZAM), N-(p-tetradecyl)azobenzenyl acrylamide (TEAZAM), N-(p-hexadecyl)azobenzenyl acrylamide (HEAZAM), and N{N-[4-(3-(5-(4-dodecyl-phenylcarbamoyl)pentyl-carbamoyl)-propyl) phenyl acrylamide (DOPPPAM), and of course, it is possible to use at least two monomers selected from the foregoing ones.

The monomer may take a form of monoclinic crystal structure, e.g., monoclinic monocrystal. The monomer takes the form of monoclinic monocrystal before the crosslinked polymer and the polymer supported reagent are prepared, and thus each monomer molecule is more regularly arranged in the polymer chain and the well arranged monomer molecules are bonded together, allowing one to obtain preferably the crosslinked polymer and the polymer supported reagent showing mesoporosity.

For obtaining the monocrystal monomer, one may add to the monomers being synthesized an agent for growing a crystal so as to grow them in the form of monocrystal. At this time, the growth rate of the monocrystal may be determined depending on the composition and the ratio of the polar solvent and the non-polar solvent being used, the time and the temperature of the crystal growth, the chemical structure and the concentration of the agent for growing crystal being added.

In addition, the monomer composition for the production of the crosslinked polymer and the polymer supported reagent may comprise the acrylamide monomer of Chemical Formula 2 alone, and it may further include at least one monomer selected from the group consisting of a styrene monomer and a vinyl monomer. The styrene monomer may be styrene or a para-alkyl (or hydroxyl) styrene derivative. The vinyl monomer may be n-alkyl(meth)acrylate or acrylonitrile.

In addition, the monomer composition essentially comprises the repeating unit of Chemical Formula 2 and optionally includes the styrene repeating unit. For example, it may comprise the two types of repeating units in a mole ratio of about 10:0 to 1:9. More specifically, when the monomer composition comprises these two monomers together, these repeating units may be included at a mole ratio of about 9:1 to 1:9, or about 5:5 to 2:8. In this case, the crosslinked polymer and the polymer supported reagent can be a copolymer comprising together the polymer repeating units such as the acrylamide repeating unit or the styrene repeating unit. As a result, when such polymer supported reagent is used for the reduction reaction of the aromatic nitro compound, it may fix and stabilize the aromatic nitro compound more, enhancing the productivity of the selective reduction reaction.

The monomer composition may be dissolved at a concentration of about 20 to 60% by weight with respect to an oil-soluble organic solvent. As the oil-soluble organic solvent, one may use benzene, toluene, xylene, cyclohexane, n-pentane, n-hexane, or the like. The monomer composition is dissolved in the oil-soluble organic solvent at a predetermined concentration to prepare the oil-soluble solution, which is then dispersed in water and subjected to a suspension polymerization, enabling the production of the polymer supported reagent with a proper size in a suitable form.

For the crosslinker, one can use any crosslinker capable of triggering a crosslinking reaction by a radical initiator. Specific examples of the crosslinker include a divinyl compound having vinyl groups bonded at both ends, a diglycidyl ether compound having an epoxy group and the like bonded at both ends capable of reacting with a secondary amine of the amide group introduced into the monomer of Chemical Formula 2. More specifically, as the crosslinker, one may use divinyl benzene, ethylene (buthylene or hexylene) glycol di(meth)acrylate, methylene (ethylene or propylene) bisacrylamide, ethylene (or polyethylene) glycol glycidyl ether, or the like.

In light of the properties of the polymer supported reagent being used in the selective reduction reaction of the aromatic nitro compound, the crosslinker may be used in an amount of about 0.1 to 5.0% by weight with respect to the weight of the monomer composition.

In addition, as the radical initiator, one may use any thermally-decomposing radical initiator known in the art to be available for the radical polymerization. Specific examples of the radical initiator include azobisisobutyronitrile (AIBN), benzoyl peroxide (BPO), and di-t-butyl peroxide (DTBP). The initiator may be used in an amount of about 0.01 to 3.0% by weight with respect to the weight of the monomer composition.

After the oil-soluble solution with the monomer composition, the radical initiator, and the crosslinker dissolved therein is obtained, it is dispersed in water with a surfactant dissolved therein and subjected to a suspension polymerization to prepare the crosslinked polymer of a uniform particle size and the polymer supported reagent.

As the surfactant, one may use any surfactant having a HLB value of about 5 to 20. For example, one may use at least one selected from a non-ionic surfactant such as polyvinyl alcohol, hydroxypropyl methyl cellulose, polyethyleneglycol alkyl ether, polyoxyethylene octyl phenyl ether, polyoxyethylene sorbitol oleate, polyoxyethylene sorbitan fatty acid ester (monolaurate, monostearate, or monoleate), or sorbitan monolaurate and an anionic surfactant such as sodium dodecyl benzene sulfonate, alone or in the mixture of at least two surfactants. The surfactant may be used in an amount of about 0.1 to 3.0% by weight with respect to the weight of the monomer composition. Using a suitable surfactant in such an amount makes it possible to produce the polymer supported reagent of a more uniform size and shape.

Besides the aforementioned surfactant, the amount of water used for dispersing the oil-soluble solution therein and the agitating speed of a stirrer used for mixing these solutions may also play a significant role so as to obtain uniformly sized and shaped particles of the polymer supported reagent. For example, the amount of water may be about 5 to 20 times the weight of the oil-soluble solution, and the agitating speed may be about 100 to 400 rpm. These conditions can be, however, properly adjusted depending on the capability of dissipating the polymerization heat released during the suspension polymerization reaction.

The temperature of the suspension polymerization for producing the aforementioned polymer supported reagent may vary with the types of the radical initiator being used, but in light of the control over the polymerization heat and the stability of the surfactant, it is preferably adjusted between about 40 and 90° C. In addition, the polymerization time may be from about 4 to 12 hours in light of the conversion rate of the polymerization and the reaction process.

Through the aforementioned suspension polymerization reaction, it is possible to prepare the crosslinked polymer having a uniform shape and a uniform size of about 20 to 300 μm and the polymer supported reagent comprising the same. In addition, the crosslinked polymer and the polymer supported reagent may include many mesopores having a uniform diameter of about 2.0 to 10.0 nm. Accordingly, as already stated in the above, the polymer supported reagent produced according to other embodiments can be preferably used in the reduction process of the aromatic nitro compound for a selective production of azoxy compounds and the like.

Thus, according to another embodiment of the present invention is provided a method of selectively reducing an aromatic nitro compound. The reduction method may comprise the step of subjecting an aromatic nitro compound to a reduction reaction in the presence of the aforementioned polymer supported reagent and a reducing catalyst.

By means of using the polymer supported reagent of the embodiment in the reduction method, an aromatic azoxy compound and the like can be produced in high yield through very simple reduction reaction process even with using a typical reducing catalyst. As such, the azoxy compound and the like, the production of which had to entail carrying out very complex processes with using an expensive catalyst, may be prepared simply and easily, and this may greatly expand the industrial applicability of the azoxy compound and the like.

In the reduction method, the reduction reaction step may comprise the steps of swelling the polymer supported reagent with a liquid aromatic nitro compound or an organic solution of an aromatic nitro compound; and subjecting the aromatic nitro compound to a reduction reaction in a solvent of water in the presence of a reducing catalyst. In addition, the reduction method may further comprise a step of extracting a reduction product from the polymer supported reagent after the reduction reaction step.

Hereinafter, the reduction method of other embodiments of the present invention will be specifically explained step by step.

First, in the reduction method, the polymer supported reagent may be swelled with the liquid aromatic nitro compound or the organic solution of the aromatic nitro compound. Through this swelling step, the aromatic ring of the aromatic nitro compound may be fixed in the mesopores of the polymer supported reagent, and this enables the selective reduction reaction of the nitro group to occur. In addition, such fixation may stabilize intermediate products such as a nitroso compound firstly generated from the reduction reaction of the aromatic nitro compound so that through the selective coupling reaction, the aromatic azoxy compound and the like may be prepared in high yield. The technological reasons for this have already been explained in the above and thus further specific explanation will be omitted.

In the swelling step and the reduction method, one may use as a reactant any aromatic nitro compound that may be fixed in the mesopores to have the foregoing effects. Specific examples of the aromatic nitro compounds include an aromatic nitro compound such as nitrobenzene, an alkyl nitrobenzene derivative such as o-methyl nitrobenzene or o-ethyl nitrobenzene, p-halogen or p-methoxy nitrobenzene, 2,5-difluoronitrobenzene, methyl-2-nitrobenzoate, 3-nitrostyrene, and 1,3-dimethyl-2-nitrobenzene. Among these compounds, one may properly use a liquid aromatic nitro compound that can readily swell the polymer supported reagent. However, it should be noted that the available one is not limited to the liquid aromatic nitro compound, and one may use any compound even in a sold sate at room temperature by dissolving the same in an aromatic organic solvent such as benzene, toluene, or xylene to form an organic solution thereof.

The amount of the reactant being used in the swelling step may be the amount corresponding to the maximum swelling ratio of the polymer supported reagent. In this way, the productivity of the reduction method may be further enhanced. In order to achieve the maximum swelling, the polymer supported reagent may be mixed with the liquid aromatic nitro compound or the organic solution of the aromatic nitro compound and subjected to swelling for 10 to 30 minutes.

After the swelling step, the polymer supported reagent swelled with the aromatic nitro compound is added to a solvent of water and subjected to the reduction reaction in the presence of a reducing catalyst.

As the reducing catalyst, any of typical reducing catalysts may be used with no limitation. For example, one may use a metal such as Zn, a Group 11 or 12 metal including Cu, Ag, Au, Cd, or Hg, or use fine particles of a Group 8 metal including Fe. Besides, it is possible to use an ionic-bond type, sold phase catalyst such as $K_4[Fe(CN)_6]$ or to use a catalyst such as $NaBH_4$. Among the catalyst, the catalyst such as $NaBH_4$ is used normally in the form of a single catalyst, but other types of catalysts may be used together with a cocatalyst. For such cocatalyst, one may use any one typically available in the reduction reaction such as $NH_4Cl$, $H_2CO_3$, $H_3PO_4$, and a diluted HCl, and besides the foregoing, other various cocatalysts may be utilized with no limitation. The cocatalyst may act as a hydrogen donor for the reduction reaction. However, in light of an economical aspect, one can properly use an inexpensive metal such as Cu, Fe, or Zn preferably in conjunction with $NH_4Cl$ as a cocatalyst. Even with using such an inexpensive reducing catalyst system, the aforementioned reduction method makes it possible to easily produce the aromatic azoxy compound and the like in high yield.

The reduction reaction step may proceed with using water as a solvent. Even when water is used as a solvent in the reduction reaction, the azoxy compound and the like may be prepared in high yield with using the polymer supported reagent of the embodiment. This can make a great contribution to the economic feasibility and the eco-friendly aspect of the reduction reaction.

The amount of water as a solvent may be about 50 to 200 times the weight of the reducing catalyst so as to sufficiently disperse the reducing catalyst and the gel particles of the swelled polymer supported reagent. As a reducing catalyst, the metal catalyst such as Zn may be used at a concentration of about 1.0 to 7.5 times the equivalent of the aromatic nitro compound as the reactant. The amount of the reducing catalyst being used, however, may vary with the types or the properties of specific reactants.

In addition, the yield of the reduced product including the azoxy compound may depend on the size and the surface area of the reducing catalyst particle, and in this respect, it is preferable to use a metal catalyst (e.g., a Zn catalyst) having a uniform particle diameter of about 50 to 200 μm. It is also preferable to use a cocatalyst in the same equivalent ratio as that of the metal catalyst including the Zn catalyst.

The temperature and the time of the reduction reaction depend on any of the foregoing reaction conditions, and for example, the reduction reaction may be conducted at a temperature of about 50 to 90° C., or about 60 to 80° C. for about 2 to 48 hours, or about 3 to 36 hours.

The reduction reaction step may be followed by a further step of extracting the reduction product such as the azoxy compound and the like from the polymer supported reagent. To this end, after the completion of the reduction reaction, a certain amount of an organic solvent immiscible with water (e.g., ethyl acetate (EA)) is added thereto and the resulting mixture is stirred for about 10 to 30 minutes and then filtered to separate as a mixed solution and a solid precipitate. Then, the mixed solution as filtered is put into a separating funnel to separate and remove the water layer, and then a drying agent such as anhydrous magnesium sulfate is added to the ethyl acetate solution to eliminate a trace amount of water remained in the solution. Then, the solvent is volatilized from the resulting solution and thereby the reduction product comprising the azoxy compound can be obtained. The structure or the yield of the reduction product may be confirmed by a Gas Chromatography (GC), a Mass analyzer (MASS), or a Column Chromatography (CC).

Moreover, in the above process, the solid precipitate being first separated is treated with an acid solution to remove an unreacted reducing catalyst therefrom, and the resulting solid is washed with a sufficient amount of water and methanol to separate the polymer supported reagent, which then may be reused.

Advantageous Effect of the Invention

As detailed in the above, the polymer supported reagent comprising a certain mesoporous crosslinked polymer is presented according to the present invention. The polymer supported reagent may be applied to the reducing process of the aromatic nitro compound and thereby expensive azoxy compounds and the like, the production of which had inevitably entailed using a rare catalyst and conducting many complicated steps, may be prepared in high yield through one simple step of the reduction process.

Moreover, the polymer supported reagent may be industrially prepared in a large scale through a simple suspension polymerization. Therefore, it can be industrially applied to the selective reduction reaction for various types of aromatic nitro compounds to synthesize at a low cost and in high yield the azoxy compound and the like, which can be utilized in various fields such as electronic materials, reducing agents, dyes, pigments, polymerization inhibitors, and the like.

DETAILS FOR PRACTICING THE INVENTION

Figure 1:
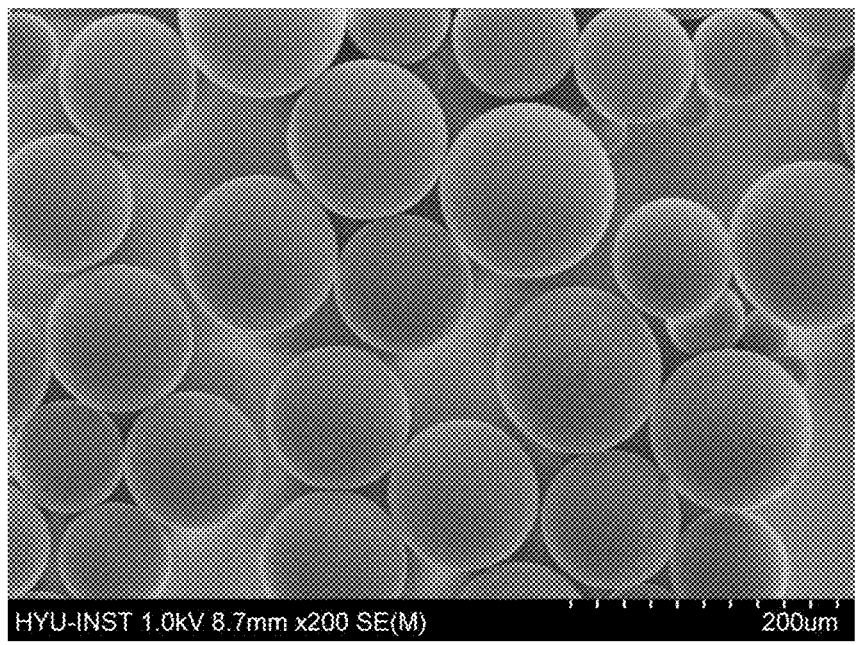
FIG. 1 is a SEM image for the particles of Polymer Supported Reagent-1 comprising the acrylamide mesoporous crosslinked polymer prepared from Example 3.

Hereinafter, the actions and the effects of the invention will be explained in further detail with reference to specific examples of the invention. However, they are merely presented by way of an example of the present invention, the scope of which shall not be defined thereby.

Examples 1 and 2

Synthesis of Acrylamide Monomers and Determination of their Crystallinity

Example 1

Synthesis of Paradodecyl Phenyl Acrylamide (DOPAM) and the Preparation of its Monocrystal First, 12 g (0.046 mol) of paradodecyl aniline was dissolved in 100 mL of THF and then put into a 100 mL three-neck round bottom flask. To the resulting mixture was added dropwise through a funnel for 10 minutes an acid remover prepared by mixing imidazole and triethyl amine at the same mole ratio (0.023 mol). Then, to the resulting mixture was slowly added dropwise through a dropping funnel over 20 minutes under a nitrogen atmosphere a solution prepared by dissolving 3.8 ml (0.047 mol) of acryloyl chloride in 20 mL of THF. At this time, the reaction mixture cooled with ice in order for its temperature to be maintained below 5° C. Thereafter, the reaction proceeded at 0° C. for 6 hours, and at 25° C. for 9 hours. After the completion of the reaction, the resulting mixture was filtered with a filtering paper to remove salt precipitates, and then the solvent was eliminated by using an evaporator. The obtained solid was dissolved in 100 mL of dichloromethane and put into a separating funnel together with 50 mL of an aqueous solution of 10% $NaHCO_3$ and shaken strongly to separate the aqueous solution layer and remove an unreacted acryloyl chloride. To the dichloromethane solution as separated was added 1.0 g of magnesium sulfate and the resulting mixture was stirred for 5 hours and filtered so as to remove a trace amount of water being dissolved in the solvent. The resulting dichloromethane solution was evaporated and then 100 mL of n-hexane was added thereto and stirred for 2 hours, and then is filtered to remove an unreacted paradodecyl aniline remained in the solution. The solvent was removed from the resulting solution by using an evaporator to provide a white solid of DOPAM (Yield: 95%). The chemical structure of DOPAM as synthesized was confirmed by a $^1$H nuclear magnetic resonance ($^1$H-NMR) spectrum, and the results are the same as follows:

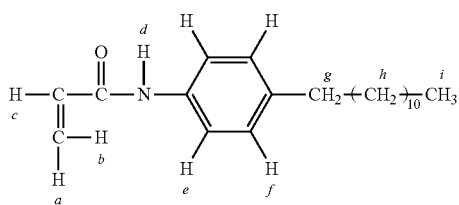

$^1$H-NMR(CDCl$_3$): e, δ7.5 (d, 2H); d, δ7.2 (s, 1H); f, δ7.15 (d, 2H); b, δ6.4 (d, 1H); c, δ6.2 (q, 1H); b, δ5.8 (d, 1H); g, δ2.6 (1, 2H); h, δ1.25-1.35 (m, 20H); i, δ0.935 (1, 3H).

Also, DOPAM as synthesized ($T_m$=101° C.) was purified again by being subjected to recrystallization with ethanol three times. The pure DOPAM as purified was put into THF and then a few drops of a non-polar solvent was added thereto, and the resulting mixture was kept at −10° C. for a certain period of time to grow a monocrystal of the monomer. At this time, the growing rate of the monocrystal was found to depend on the composition and the ratio of the polar and non-polar solvents as being used, the time and the temperature for crystal growth, the chemical structure and the concentration of the crystal growing agent as being added.

The crystal structure of the monocrystal obtained in Example 1 was analyzed by using the X-ray diffractometry, providing the crystallographic data of the monocrystal as set forth in Table 1. Based on such crystallographic data, the monocrystal of the monomer of Example 1 was confirmed to have a monoclinic crystal structure.

TABLE 1

| Crystallographic data for the monocrystal of the monomer obtained from Example 1 | |
|---|---|
| Empirical formula | C$_{21}$H$_{33}$N$_1$O$_1$ |
| Formula weight | 315.48 |
| Temperature [K] | 293(2) K |
| Wavelength [Å] | 0.71073 |
| Crystal system, space group | Monoclinic, P2$_1$/c |
| a [Å] | 4.7055(13) |
| b [Å] | 43.315(16) |
| c [Å] | 9.4150(19) |
| β[°] | 95.158(19) |
| Volume [Å$^3$] | 1911.2(10) |
| d$_{calcd}$ [gcm$^{-3}$] | 1.096 |
| μ[mm$^{-1}$] | 0.066 |
| F(000) | 696 |
| Crystal size [mm] | 0.55 × 0.30 × 0.25 |
| θ range [°] | 1.88-26.33 |
| Data/parameters | 1845/213 |
| GOF on F$^2$ | 1.111 |
| R1, wR2 [I > 2σ(I)] | 0.0975, 0.2551 |
| Largest diff. peak and hole [e · Å$^{-3}$] | 0.358 and −0.343 |

Example 2

Synthesis of Paratetradecyl Phenyl Acrylamide (TEPAM) and Parahexadecyl Phenyl Acrylamide (HEPAM) and Preparation of their Monocrystals In addition, TEPAM and HEPAM were synthesized in the same manner as set forth in Example 1 except for using paratetradecy aniline having 14 carbon atoms and parahexadecyl aniline having 16 carbon atoms instead of paradodecyl aniline having 12 carbon atoms being used in Example 1. The yields for each compound were 90% and 93%, respectively. Monocrystals of TEPAM and HEPAM were grown in the same manner as Example 1, and the results obtained by using the XRD analysis technique confirmed that the monocrystals have a monoclinic crystal structure.

Examples 3 to 5

Preparation of the Acrylamide Mesoporous Crosslinked Polymer and the Polymer Supported Reagent Example 3

Preparation of the Particles of Polymer Supported Reagent-1

3.0 g of the DOPAM monomer having a rod like crystal shape prepared from Example 1, 0.03 g of divinyl benzene as a crosslinker, and 12.0 mg of AIBN as a radical initiator were put into 15 mL of benzene and stirred to prepare a monomer solution in advance. As a surfactant, 0.6 g of polyoxyethylene sorbitan monolaurate and 0.6 g of sorbitan monolaurate, and 120 mL of distilled water were put into a 250 mL 3-neck flask equipped with a mechanical stirrer and stirred to make a homogeneous aqueous solution. To this aqueous solution was added a previously prepared monomer solution and the resulting mixture was stirred at 30° C. for 20 minutes at 250 rpm, then subjected to a suspension polymerization at 70° C. of 9 hours. After the completion of the polymerization reaction, the suspension polymerization product dispersed in water was precipitated with a sufficient amount of methanol and filtered to provide solid particles. The solid particles were dried in a vacuum oven for 12 hours to obtain the powder of Polymer supported reagent-1 comprising the acrylamide mesoporous crosslinked polymer. The powders of Polymer supported reagent-1 as obtained were in the form of spherical particles having a size of about 80 to 130 μm, and their picture taken by the scanning electron microscope (SEM) is shown in FIG. 1. In addition, the results of analysis with a computer program, Cerius Program, capable of analyzing a three dimensional structure of the molecules reveal that the powders of Polymer supported reagent-1 comprise many mesopores having a diameter of 2.5 to 3.5 nm.

For conducting a selective reduction reaction for an aromatic nitro compound, the swelling ratio of Polymer supported reagent-1 of crosslinked polymer as prepared was measured for the aromatic nitro compound. That is, 2.0 g of the dried particles of Polymer supported reagent-1 were put into a flask containing 20 mL of benzene or an aromatic nitro compound (e.g., nitrobenzene, o-methyl nitrobenzene, or o-ethyl nitrobenzene and stirred for 1 hour. Polymer supported reagent-1 being swelled was filtered for 10 minutes by using a stainless sieve (100 mesh) and then the weight of the swelled gel was measured. The measured weights were divided by the weight of the dried polymer supported reagent to calculate the swelling ratios of Polymer supported reagent-1 for benzene and the aromatic nitro compounds.

The swelling ratios of Polymer supported reagent-1 for benzene, nitrobenzene, o-methyl nitrobenzene, and o-ethyl nitrobenzene were found to be 10.5, 14.6, 12.5, and 16.3 times, respectively.

Example 4

Preparation of Polymer Supported Reagent-2

Figure 2:
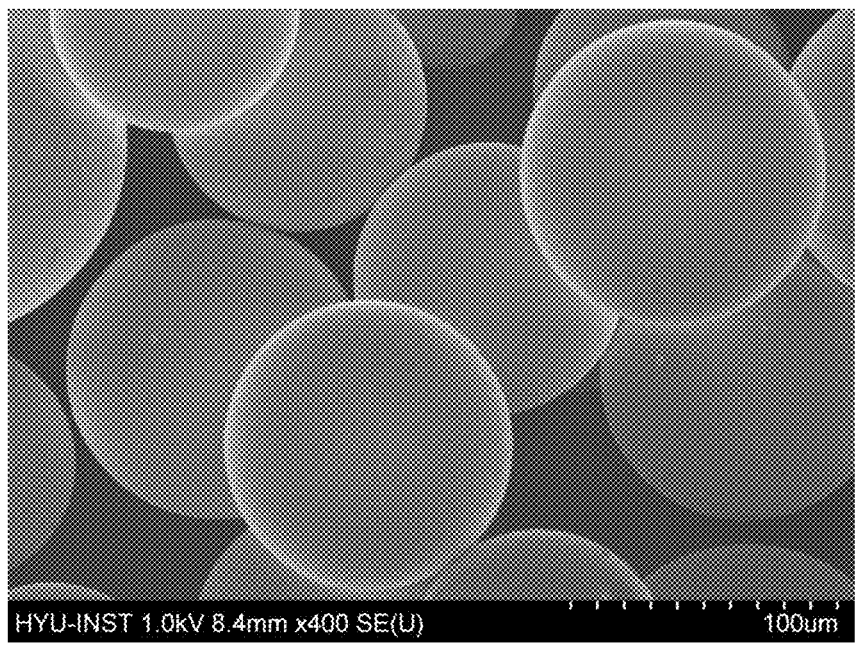
FIG. 2 is a SEM image for the particles of Polymer Supported Reagent-2 comprising the acrylamide mesoporous crosslinked polymer prepared from Example 4.

Except that 1.0 g of DOPAM, 1.33 g of styrene, 0.023 g of divinyl benzene, and 9.3 mg of AIBN were put into 10 mL of benzene to prepare a monomer solution and 0.4 g of polyoxyethylene sorbitan monolaurate and 0.4 g of sorbitan monolaurate were put into 80 mL of water to prepare an aqueous solution of a surfactant, Polymer supported reagent-2 was obtained in the same manner as set forth in Example 3. The powders of Polymer supported reagent-2 as obtained were spherical particles having a uniform size of about 100 to 120 µm, and their picture taken by SEM is shown in FIG. 2. In addition, the results of analysis with a computer program, Cerius Program, capable of analyzing a three-dimensional structure of the molecules reveal that the powders of Polymer supported reagent-2 comprise many mesopores having a diameter of 2.0 to 2.5 nm.

The swelling ratios of Polymer supported reagent-2 for benzene, nitrobenzene, o-methyl nitrobenzene, and o-ethyl nitrobenzene were found to be 13.3, 17.9, 15.9, and 18.0 times, respectively.

Example 5

Preparation of Polymer Supported Reagent-3

Figure 3:
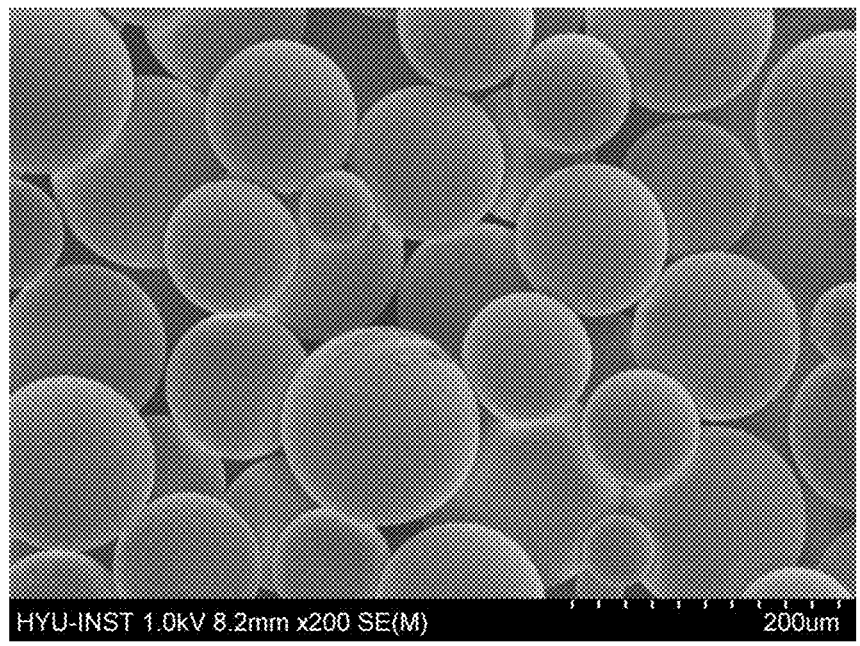
FIG. 3 is a SEM image for the particles of Polymer Supported Reagent-3 comprising the acrylamide mesoporous crosslinked polymer prepared from Example 5.

Except that 1.5 g of DOPAM, 0.5 g of styrene, 0.02 g of divinyl benzene, and 8.0 mg of AIBN were put into 10 mL of benzene to prepare a monomer solution and 0.4 g of polyoxyethylene sorbitan monolaurate and 0.4 g of sorbitan monolaurate were put into 80 mL of water to prepare an aqueous solution of a surfactant, Polymer supported reagent-3 was obtained in the same manner as set forth in Example 3. The powders of Polymer supported reagent-3 as obtained were spherical particles having a size of about 50 to 145 µm, and their picture taken by SEM is shown in FIG. 3. In addition, the results of analysis with a computer program, Cerius Program, capable of analyzing a three dimensional structure of the molecules reveal that the powders of Polymer supported reagent-3 comprise many mesopores having a diameter of 2.0 to 3.0 nm.

The swelling ratios of Polymer supported reagent-3 for benzene, nitrobenzene, o-methyl nitrobenzene, and o-ethyl nitrobenzene were found to be 11.3, 15.6, 13.9 and 16.8 times, respectively.

Comparative Example 1

Figure 4:
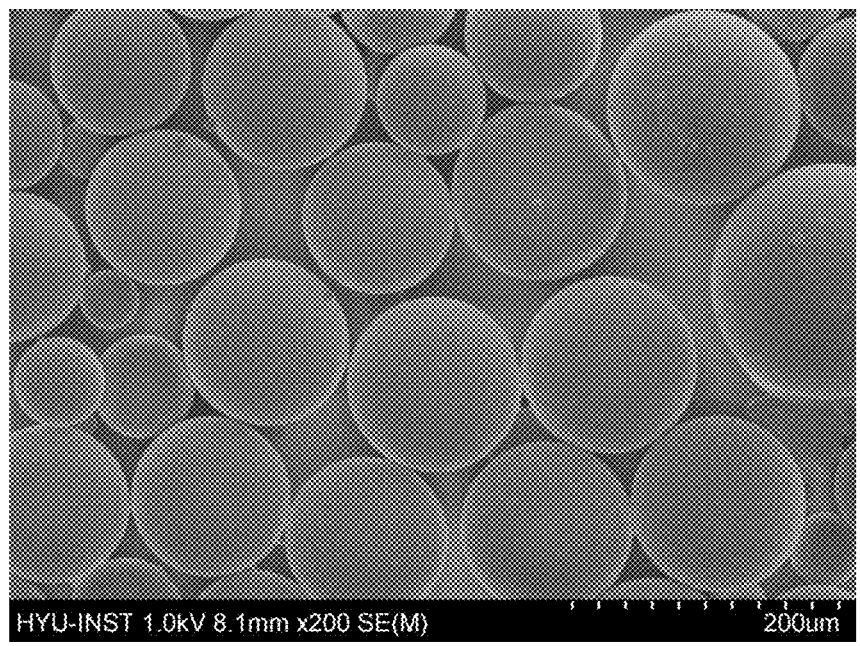
FIG. 4 is a SEM image for the particles of a polymer supported reagent based on a polystyrene crosslinked polymer, which was prepared from Comparative Example 1.

Preparation of Polymer Supported Reagent Particles Based on a Polystyrene Crosslinked Polymer A polymer supported reagent based on a polystyrene crosslinked polymer from a conventional styrene monomer was prepared for comparison with the polymer supported reagent of Examples 3 to 5 being used in the selective reduction reaction for the aromatic nitro compound. Except that 5.0 g of styrene, 0.05 g of divinyl benzene, and 20.0 mg of AIBN were put into 10 mL of benzene to prepare a monomer solution and 0.4 g of polyoxyethylene sorbitan monolaurate and 0.4 g of sorbitan monolaurate were put into 80 mL of water to prepare an aqueous solution of a surfactant, the polymer supported reagent based on a polystyrene crosslinked polymer was obtained in the same manner as set forth in Example 3. The powders of the polymer supported reagent as obtained were found to be spherical particles having a size of about 60 to 150 µm, and their picture taken by SEM is shown in FIG. 4.

The swelling ratios of the polymer supported reagent of Comparative Example 1 for benzene, nitrobenzene, o-methyl nitrobenzene, and o-ethyl nitrobenzene were found to be 9.2, 13.1, 10.8 and 14.2 times, respectively.

By using Polymer supported reagents-1, Polymer supported reagents-2, and Polymer supported reagents-3, each comprising the acrylamide mesoporous crosslinked polymers of Examples 3 to 5, respectively, novel reduction reactions for an aromatic nitro compound by means of the conventional catalyst, $Zn/NH_4Cl$, were implemented in water. The reduction reactions were carried out with Polymer supported reagent-1 of Example 3 and Polymer supported reagent-2 of Example 4 having the largest swelling ratio for the aromatic nitro compounds. Hereinbelow, Examples 6, 7, and 8 are directed to the examples of the reduction reaction for representative aromatic nitro compounds, i.e., nitrobenzene, methyl nitrobenzene, and ethyl nitrobenzene. In addition, Examples 9, 10, and 11 are directed to the representative examples of the reduction reactions for a mixture of two types of alkyl nitrobenzene derivatives.

Example 6

Selective Reduction Reaction for Nitrobenzene by Using the Polymer Supported Reagent 0.204 mL (2.0 mmol) of nitrobenzene and either of 17.2 mg (the amount required for swelling of the reactant, nitrobenzene, in 100%) of Polymer supported reagent-1 synthesized in Example 3 or 14 mg (the amount required for swelling of the reactant, nitrobenzene, in 100%) of Polymer supported reagent-2 synthesized in Example 4 were put into a 50 mL, two-neck flask equipped with a water cooler, and the resulting mixture was stirred at a nitrogen atmosphere for 20 minutes to swell the the polymer supported reagent with the reactant. To this were added 0.262 g (4.0 mmol) of Zn powders, 0.214 g (4.0 mmol) of $NH_4Cl$, and 15 mL of distilled water, and then the reduction reaction was conducted at 80° C. for 200 minutes. After the completion of the reaction, 30 mL of an organic solvent, EA was added thereto and stirred at room temperature for 30 minutes. The resulting mixture was then filtered to separate firstly the solid mixture and the liquid mixture solution. The liquid mixture solution as obtained was put into a separating funnel to separate a water layer and an EA layer. To the separated water layer was added 20 mL of EA and stirred to extract the product remained in the water layer. This procedure was repeated 3 times. To the EA solution as combined was added 1.0 g of anhydrous magnesium sulfate and the resulting mixture was stirred for 30 minutes and then filtered. From the filtered EA solution, an excessive amount of EA was evaporated by using an evaporator to obtain azoxybenzene as a main product.

Besides the aforementioned representative reaction, the same type of the reduction reactions were conducted in the same manner under different reaction conditions such as a catalyst condition for the reduction reaction, a reaction temperature, and a reaction time. The reaction conditions for carrying out the reactions are summarized in 6-1 to 6-9 of Table 1. The yields of the products as varied with changing the reaction conditions are also summarized in 6-1 to 6-9 of Table 2.

Example 7

Selective Reduction Reaction for Ethyl Nitrobenzene by Using the Polymer Supported Reagent The reduction reaction was carried out in the same manner as set forth in Example 6 except for using 2.0 mmol of ethyl nitrobenzene instead of nitrobenzene and using 19 mg (the amount required for swelling of the reactant in 100%) of Polymer supported reagent-2, and thereby diethyl azoxybenzene of a symmetrical structure was obtained as a main product. The conditions for the reduction reaction of ethyl nitrobenzene by using the polymer supported reagent and the yields of the products are summarized in 7-1 to 7-3 of Table 1 and 7-1 to 7-3 of Table 2, respectively.

Example 8

Selective Reduction Reaction for Methyl Nitrobenzene by Using the Polymer Supported Reagent The reduction reaction was carried out in the same manner as set forth in Example 6 except for using 2.0 mmol of methyl nitrobenzene instead of nitrobenzene and using 20 mg (the amount required for swelling of the reactant in 100%) of Polymer supported reagent-2, and thereby dimethyl azoxybenzene having a symmetrical structure was obtained as a main product. The conditions for the reduction reaction of methyl nitrobenzene by using the polymer supported reagent and the yields of the products are summarized in 8-1 to 8-2 of Table 1 and 8-1 to 8-2 of Table 2.

Example 9

Selective Reduction Reaction for a Mixture of Nitrobenzene/Ethyl Nitrobenzene by Using the Polymer Supported Reagent The reduction reaction was carried out in the same manner as set forth in Example 6 except for using a mixture of 1.0 mmol of nitrobenzene and 1.0 mmol of o-ethyl nitrobenzene instead of using nitrobenzene alone, and using 16.5 mg (the amount required for swelling of the reactant, i.e., the mixture, in 100%) of Polymer supported reagent-2, and thereby an azoxybenzene derivative of a symmetrical structure and an azoxybenzene derivative of an asymmetrical structure were obtained as a main product, respectively. Besides, a small amount of an azobenzene derivative of a symmetrical structure was also synthesized.

Example 10

Selective Reduction Reaction for a Mixture of Nitrobenzene/Methyl Nitrobenzene by Using the Polymer Supported Reagent The reduction reaction was carried out in the same manner as set forth in Example 6 except for using a mixture of 1.0 mmol of nitrobenzene and 1.0 mmol of o-methyl nitrobenzene instead of using nitrobenzene alone, and using 17 mg (the amount required for swelling of the reactant, i.e., the mixture, in 100%) of Polymer supported reagent-2, and thereby an azoxybenzene derivative of a symmetrical structure and an azoxybenzene derivative of an asymmetrical structure were obtained as a main product, respectively.

Example 11

Selective Reduction Reaction for a Mixture of Methyl Nitrobenzene/Ethyl Nitrobenzene by Using the Polymer Supported Reagent The reduction reaction was carried out in the same manner as set forth in Example 6 except for using a mixture of 1.0 mmol of o-methyl nitrobenzene and 1.0 mmol of o-ethyl nitrobenzene instead of using nitrobenzene alone, and using 19.5 mg (the amount required for swelling of the reactant in 100%) of Polymer supported reagent-2, and thereby an azoxybenzene derivative of a symmetrical structure and an azoxybenzene derivative of an asymmetrical structure were obtained as a main product, respectively.

The conditions of the aforementioned reduction reactions of Examples 9 to 11 for a mixture of alkyl nitrobenzenes by using the polymer supported reagent and the yields of the products are summarized in Table 3 and Table 4, respectively. In addition, the chemical structures of the azobenzene or azoxybenzene derivatives synthesized from Examples 9 to 11 having a symmetrical or asymmetrical structure are shown in Table 5 and Table 6, respectively.

Further, in order to identify the yields and the chemical structures of the products synthesized in the reduction reactions for the aromatic nitro compound by using the aforementioned polymer supported reagent, the following separation techniques and the following analysis techniques were adopted. After the GC spectrums for the mixed products being obtained from the reduction reaction were measured, the elution time and the elution area for each product analyzed in the spectrum were compared with the values for 1,3,5-trimethoxy benzene being used as a standard substance and thereby the types and the yields of the synthesized products were qualitatively estimated. Moreover, by using a column chromatography (CC) technique, each of pure products was separated from the mixed products obtained from the reaction and the yield of each product was quantitatively determined. Besides, mass spectrums and H-NMR spectrums were measured for each of the products being separated and used to determine an accurate chemical structure for the product through an analysis of the mass and the characteristic peaks for the synthesized product.

Figure 5:
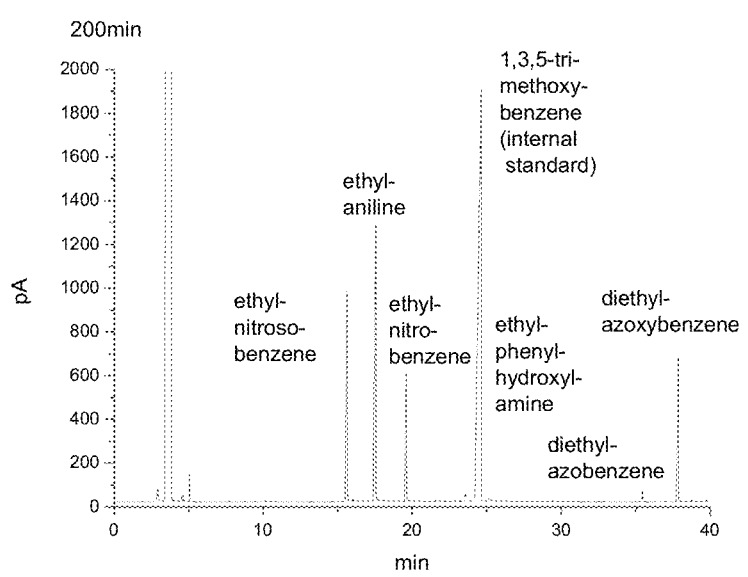
FIG. 5 is a representative GC spectrum for a mixture of the products prior to being separated that were obtained from the reduction reaction of o-ethyl nitrobenzene carried out under the conditions of Example 7-1 as set forth in Table 1.
Figure 6A:
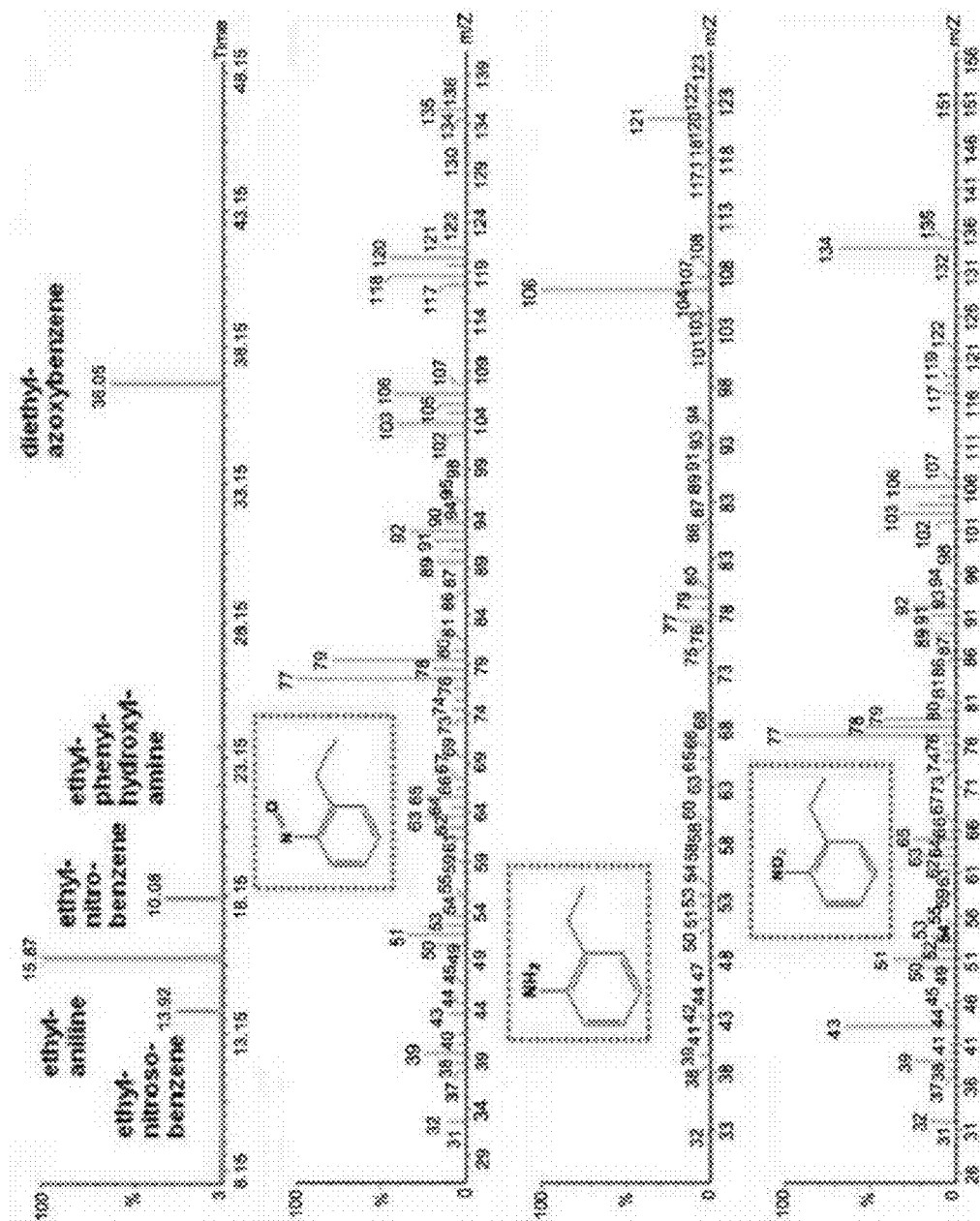
FIG. 6 is a representative GC-MASS spectrum for a mixture of the products prior to being separated that were obtained from the reduction reaction of o-ethyl nitrobenzene carried out under the conditions of Example 7-1 as set forth in Table 1.
Figure 6B:
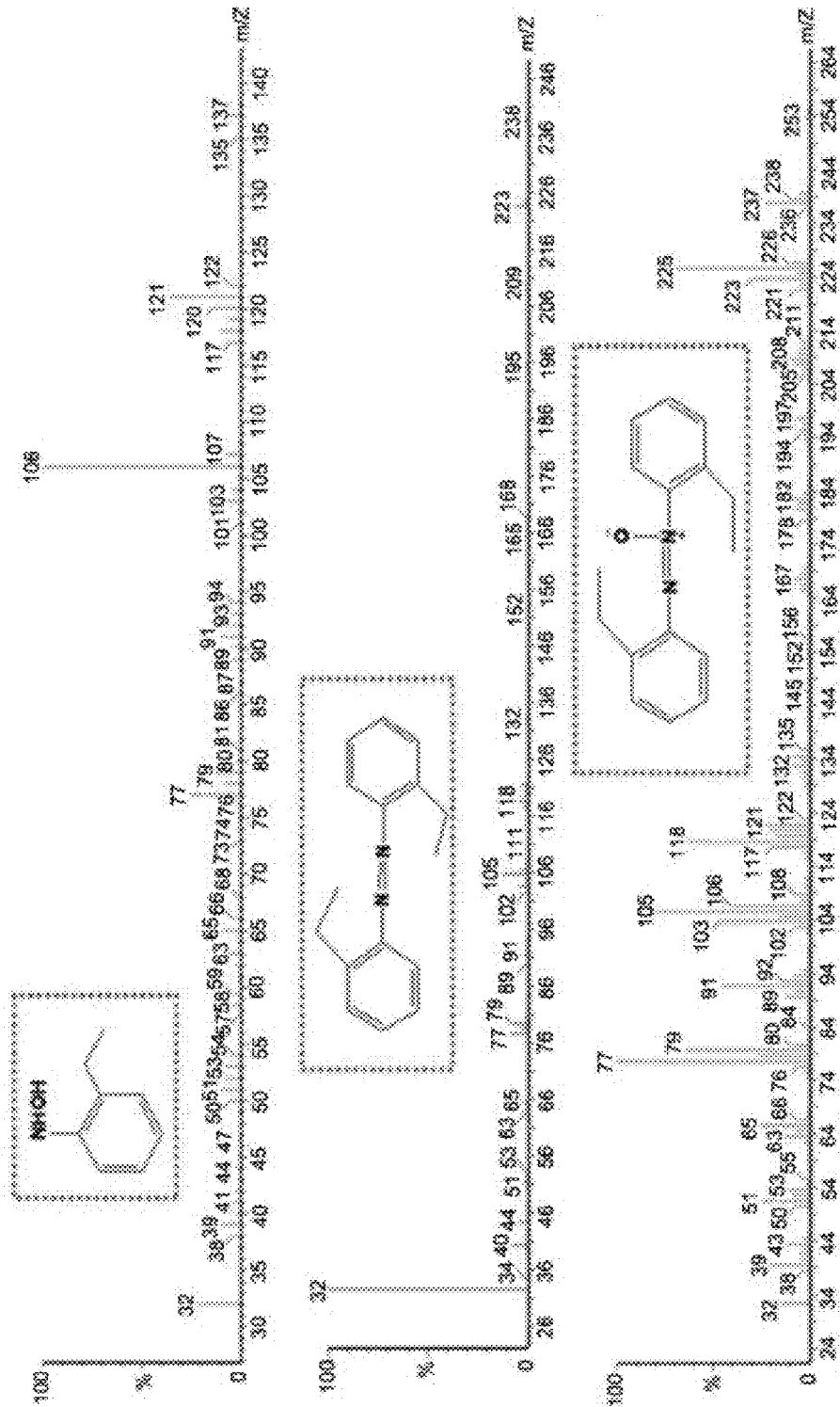
Figure 7:
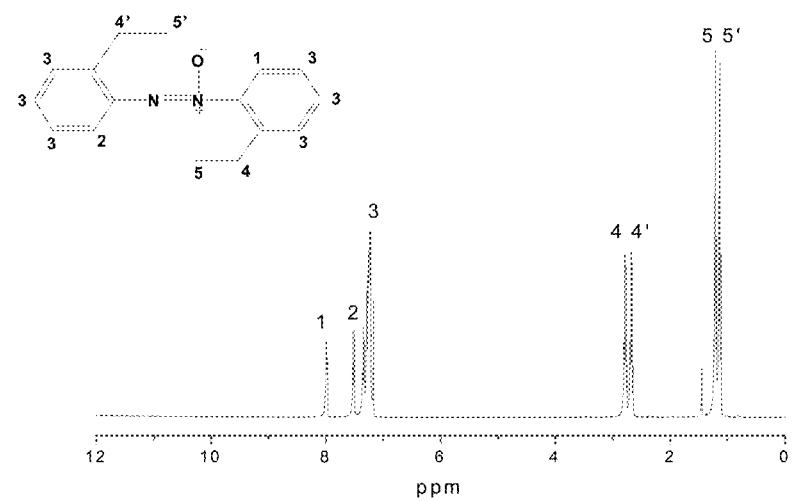
FIG. 7 is a representative H-NMR spectrum for diethyl azoxybenzene of a symmetrical structure that was obtained as a main product from the reduction reaction of o-ethyl nitrobenzene carried out under the conditions of Example 7-1 as set forth in Table 1.
Figure 8A:
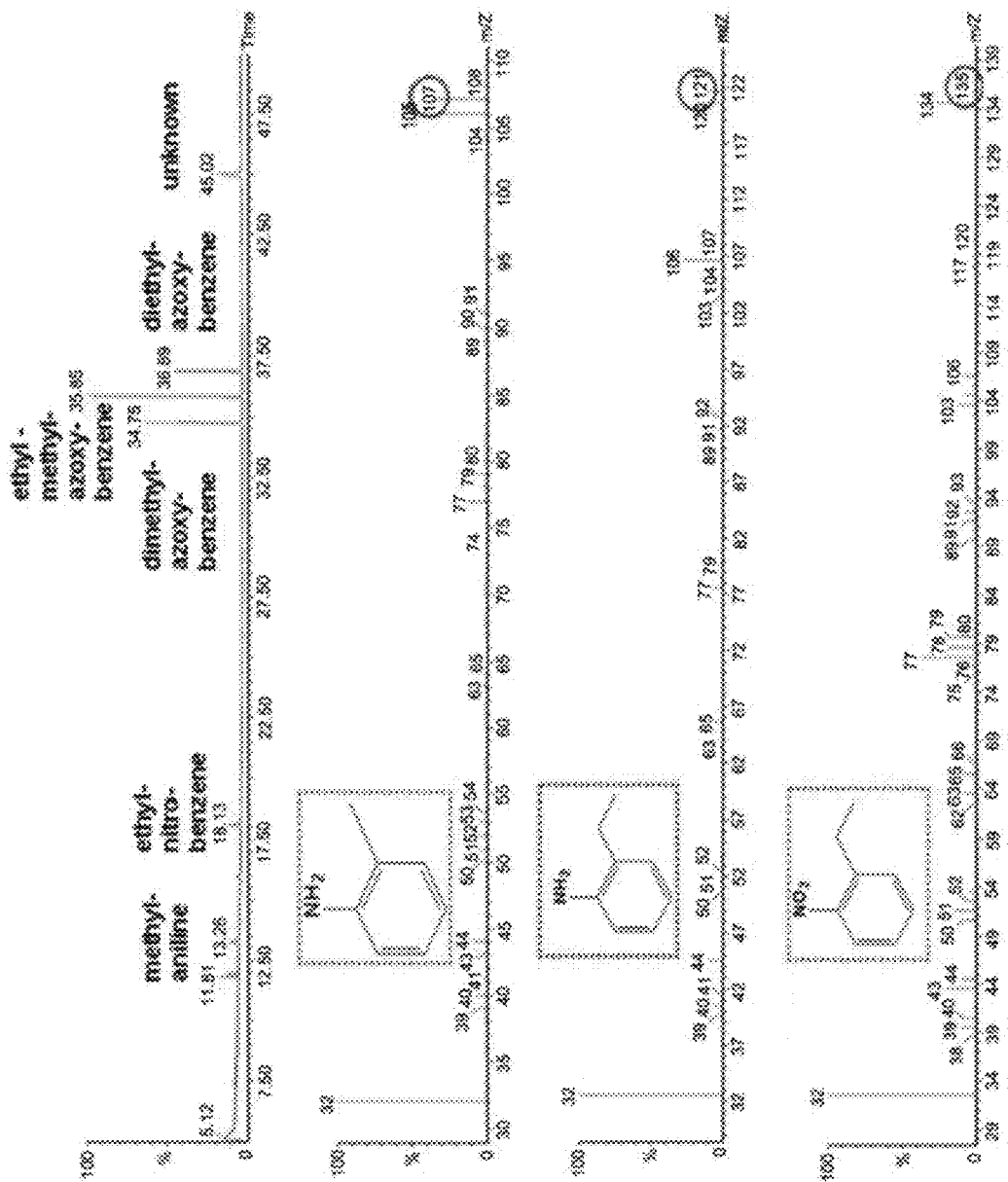
FIG. 8 is a representative GC-MASS spectrum for a mixture of the products prior to being separated that were obtained from the reduction reaction of a mixture of alkyl nitrobenzenes carried out under the conditions of Example 11 as set forth in Table 3.
Figure 8B:
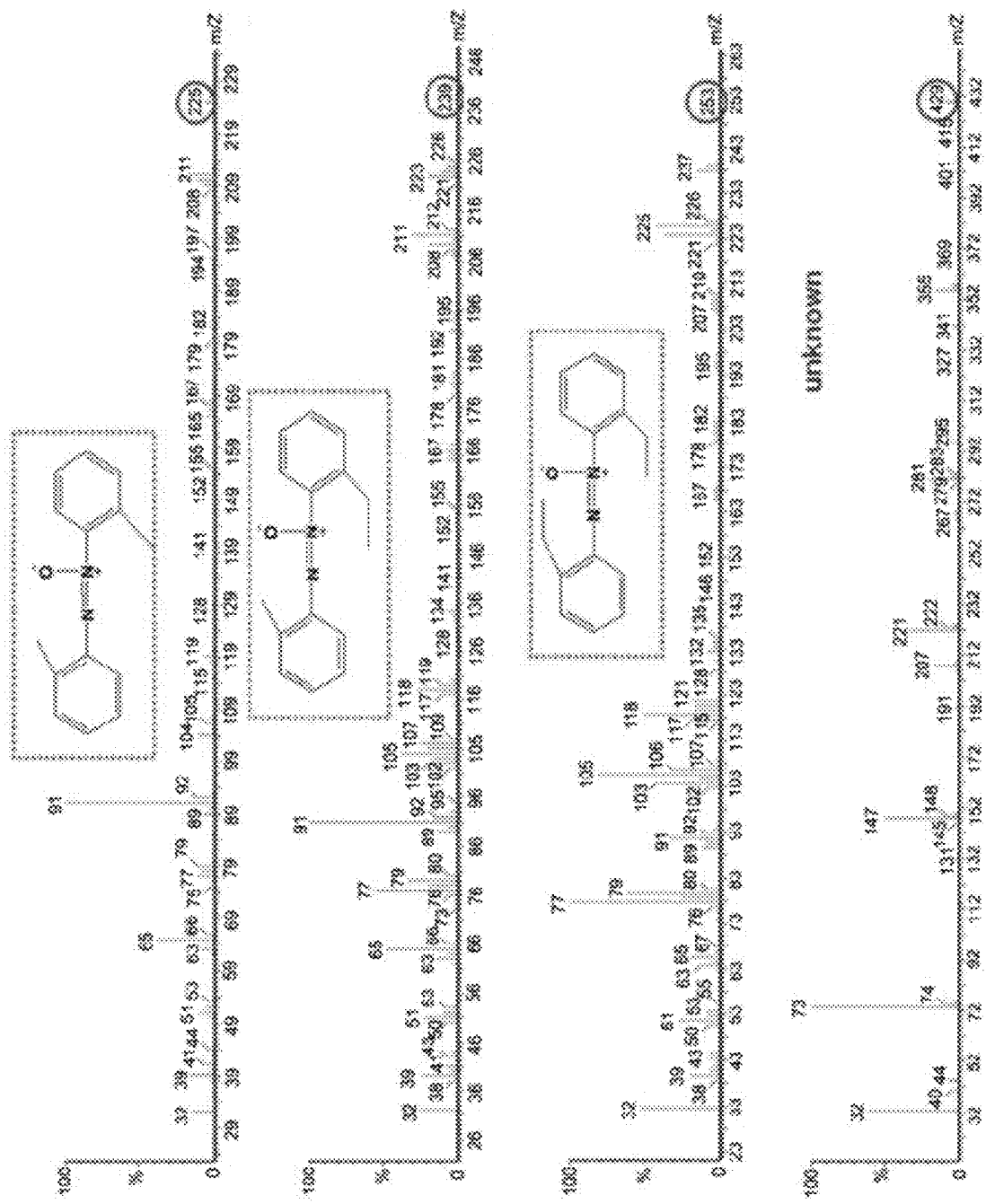
Figure 9:
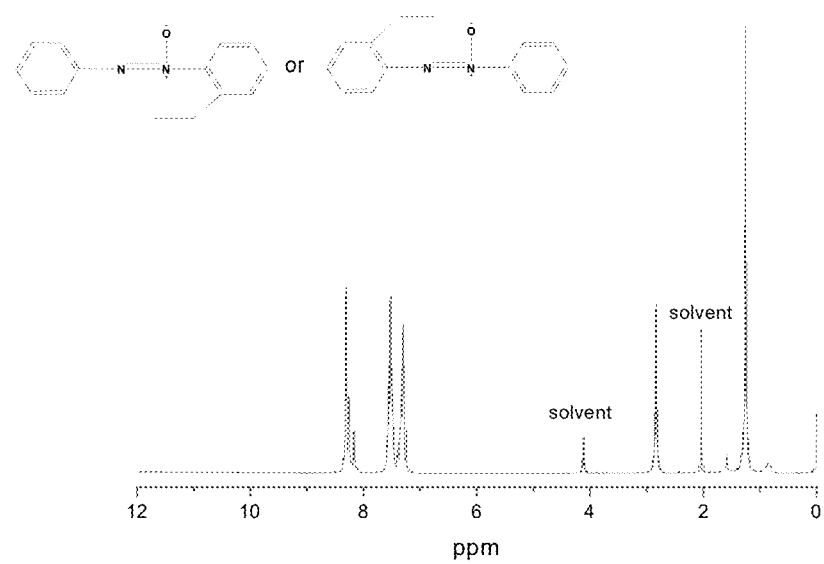
FIG. 9 is a representative H-NMR spectrum for the alkyl azoxybenzene of an asymmetrical structure that was obtained as a main product from the reduction reaction of a mixture of alkyl nitrobenzenes carried out under the conditions of Example 9 as set forth in Table 3.

FIG. 5 and FIG. 6 show representative GC and GC-mass spectrums for the products synthesized from the reduction reaction of ethyl nitrobenzene. FIG. 7 shows a representative H-NMR spectrum for diethyl azoxybenzene of a symmetrical structure, the representative main product synthesized through the aforementioned selective reduction reaction of ethyl nitrobenzene. FIG. 8 is a representative GC-MASS spectrum for the products of an asymmetrical structure synthesized from the reduction reaction of the alkyl nitrobenzene mixture of Example 11. FIG. 9 is a representative H-NMR spectrum of the alkyl azoxybenzene of an asymmetrical structure, which was synthesized in Example 9 and shown as a main product in Table 6.

Comparative Example 2

Reduction Reaction of Nitrobenzene by Using a Polymer Supported Reagent Based on a Polystyrene Crosslinked Polymer The reduction reaction was carried out in the same manner as set forth in Example 6 except for using 19.1 mg (the amount required for swelling of the reactant in 100%) of the polymer supported reagent based on a polystyrene crosslinked polymer prepared from Comparative Example 1 instead of using Polymer supported reagent-2 prepared from Example 4, and thereby azoxybenzene was obtained as a main product in a yield of about 46%.

TABLE 1

Reaction conditions[a] for the reduction reaction of alkyl nitrobenzenes by using the polymer supported reagent

| Example | reactant | conditions for catalyst[b] (mole ratio) | reaction temperature (° C.) | reaction time (minutes) |
| --- | --- | --- | --- | --- |
| 6-1 | nitrobenzene | 1/2/2 | 60 | 200 |
| 6-2 | nitrobenzene | 1/2/2 | 80 | 200 |
| 6-3 | nitrobenzene | 1/2/2 | 80 | 24 hours |
| 6-4 | nitrobenzene | 1/3/3 | 60 | 200 |
| 6-5 | nitrobenzene | 1/3/3 | 80 | 200 |
| 6-6 | nitrobenzene | 1/2/1 | 80 | 200 |
| 6-7[c] | nitrobenzene | 1/2/1 | 80 | 200 |
| 6-8[d] | nitrobenzene | 1/2/2 | 80 | 200 |
| 6-9[d] | nitrobenzene | 1/2/2 | 80 | 6 hours |
| Comp. Example-2[e] | nitrobenzene | 1/2/1 | 80 | 200 |
| 7-1 | o-ethyl nitrobenzene | 1/2/2 | 80 | 200 |
| 7-2 | o-ethyl nitrobenzene | 1/2/2 | 80 | 24 hours |
| 7-3 | o-ethyl nitrobenzene | 1/3/3 | 80 | 200 |
| 8-1 | o-methyl nitrobenzene | 1/2/2 | 80 | 200 |
| 8-2 | o-methyl nitrobenzene | 1/2/2 | 80 | 24 hours |

[a]except for 6-8, 6-9, and Comparative Example 2 as particularly mentioned, Polymer supported reagent-2 as newly prepared in Example 4 was used

[b][Reactant]/[Zn]/[NH$_4$Cl] = mole ratio

[c]Polymer supported reagent-2 that had been used in the reduction reaction of Example 6 was recovered and reused.

[d]Polymer supported reagent-1 as newly prepared in Example 3 was used

[e]Polymer supported reagent based on a polystyrene crosslinked polymer synthesized in Comparative Example 1 was used

TABLE 2

Yield of the products for the reduction reaction of alkyl nitrobenzenes by using polymer supported reagents

| | | Product Yield (%) | | | | |
| --- | --- | --- | --- | --- | --- | --- |
| Example | conversion[a] (%) | nitrosobenzene derivative | aniline derivative | phenyl hydroxylamine derivative | azobenzene derivative | azoxybenzene derivative |
| 6-1 | 78 | 1 | 1 | 2 | 0 | 74 |
| 6-2 | 79 | 0 | 2 | 0 | 0 | 77 |
| 6-3 | 100 | 0 | 0 | 0 | 0 | 100 |
| 6-4 | 90 | 2 | 3 | 5 | 0 | 80 |
| 6-5 | 95 | 3 | 3 | 5 | 0 | 84 |
| 6-6 | 77 | 0 | 1 | 0 | 0 | 76 |
| 6-7 | 76 | 0 | 3 | 0 | 0 | 73 |
| 6-8 | 95 | 12 | 11 | 0 | 2 | 70 |
| 6-9 | 100 | 8 | 7 | 0 | 2 | 83 |
| Comp. Example-2 | 65 | 5 | 7 | 7 | 0 | 46 |
| 7-1 | 95 | 32 | 32 | 0 | 7 | 24 |
| 7-2 | 92 | 0 | 8 | 0 | 0 | 84 |
| 7-3 | 90 | 24 | 45 | 0 | 2 | 19 |
| 8-1 | 94 | 38 | 38 | 0 | 0 | 18 |
| 8-2 | 96 | 0 | 5 | 0 | 0 | 91 |

[a] Ratio of the reactant being converted into the product

The results of Table 1 and Table 2 reveal that when the polymer supported reagents comprising acrylamide mesoporous crosslinked polymers of the examples were used, the yield of the main product, azoxybenzene, was at least two times higher than when the polymer supported reagent based on a polystyrene crosslinked polymer from the comparative example being used (see Examples 6 and 7). In addition, the results of Table 1 and Table 2 show that even very simple reduction reaction of a single stage alone may produce an expensive product of azoxybenzene in high yield. These results confirmed that the polymer supported reagents of the examples are far more effective in the selective reduction reaction of the aromatic nitro compound.

TABLE 3

Reaction conditions[a] for the reduction reaction of a mixture of alkyl nitrobenzenes by using the polymer supported reagents

| Example | reactant[b] | conditions for catalyst[c] | reaction temperature (□) | reaction time (hours) |
|---|---|---|---|---|
| 9 | nitrobenzene (A) o-ethyl nitrobenzene (B) | 1/2/2 | 80 | 24 |
| 10 | nitrobenzene (A) o-methyl nitrobenzene (C) | 1/2/2 | 80 | 24 |
| 11 | o-methyl nitrobenzene (C) o-ethyl nitrobenzene (B) | 1/2/2 | 80 | 24 |

[a] Particles of Polymer supported reagent-2 as newly prepared in Example 4 were used
[b] A mixture of two types of alkyl nitrobenzenes having different structures was used
[c] [Reactant]/[Zn]/[NH$_4$Cl] = mole ratio.

TABLE 4

Yield of the products for the reduction reaction of a mixture of alkyl nitrobenzenes by using polymer supported reagents

| | | Product Yield (%) | | | |
|---|---|---|---|---|---|
| Example | conversion[a] (%) | aniline derivative[b] | azobenzene derivative of symmetrical structure[c] | azoxybenzene derivative of symmetrical structure[d] | azoxybenzene derivative of asymmetrical structure[e] |
| 9 | 95 | A (0) B (0) | AA (2) BB (7) | AA (40) BB (15) | AB or BA (31) |
| 10 | 98 | A (0) C (0) | AA (0) CC (0) | AA (63) CC (4) | AC or CA (31) |
| 11 | 100 | C (0) B (1) | CC (0) BB (0) | CC (24) BB (20) | CB or BC (55) |

[a] ratio of the reactant being converted into a product
[b] aniline derivatives derived from reactant A, B, and C: A = aniline, B = o-ethyl aniline, C = o-methyl aniline
[c] Chemical structures for the products of the symmetrical structure derived from reactant A, reactant B, and reactant C are shown in Table 5
[d] Chemical structures for the products of the asymmetrical structure derived from reactant A, reactant B, and reactant C are shown in Table 6

TABLE 5

Chemical Structure of azobenzene or azoxybenzene derivatives of symmetrical structure derived from the reduction reactions of a mixture of alkyl nitrobenzenes by using the polymer supported reagents
Compounds of symmetrical structure

| notation | azobenzene derivative | azoxybenzene derivative |
|---|---|---|
| AA | azobenzene | azoxybenzene |
| BB | diethyl azobenzene | diethyl azoxybenzene |
| CC | dimethyl azobenzene | dimethyl azoxybenzene |

TABLE 6

Chemical Structure of azobenzene or azoxybenzene derivatives of asymmetrical structure derived from the reduction reactions of a mixture of alkyl nitrobenzenes by using the polymer supported reagents
Compounds of asymmetrical structure

| Example | azobenzene derivative | | azoxybenzene derivative | |
|---|---|---|---|---|
| 9 | ethyl azobenzene (BA) 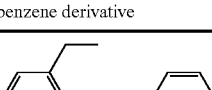 | ethyl azoxybenzene (AB) 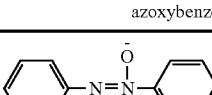 | ethyl azoxybenzene (BA) 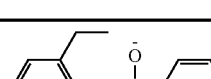 | |
| 10 | methyl azobenzene (CA)  | methyl azoxybenzene (AC) 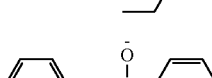 | methyl azoxybenzene (CA) 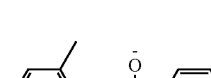 | |
| 11 | ethyl methyl azobenzene (BC)  | ethyl methyl azoxybenzene (CB) 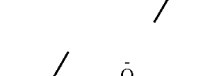 | ethyl methyl azoxybenzene (BC) 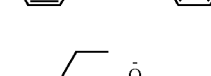 | |

The results of Tables 3 to 6 show that using the polymer supported reagent may easily produce not only the azoxybenzene derivatives of the symmetrical structure but also the derivatives of the asymmetrical structure in high yield. In addition, the azoxybenzene derivative of a desired asymmetrical structure may be selectively prepared by adjusting the reaction conditions.

What is claimed is:

1. A polymer supported reagent comprising an acrylamide mesoporous crosslinked polymer including at least one repeating unit of Chemical Formula 1:

[Chemical Formula 1]

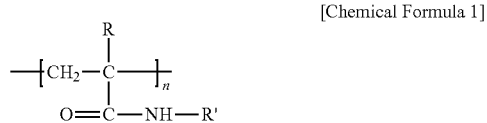

in Chemical Formula 1, n is an integer of 15 to 1800,
R is hydrogen or methyl,
R' is X,

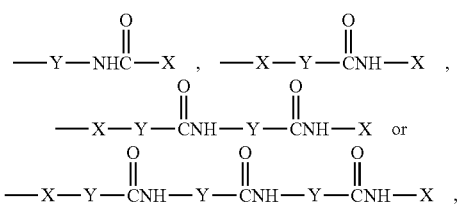

X is —Z—R",
Y is an alkylene of C1 to C10,
Z is an arylene of C6 to C20, and
R" is a linear or branched hydrocarbon of C10 to C20, or a linear or branched perfluorohydrocarbon of C10 to C20.
wherein the polymer supported reagent comprises a plurality of pores having a diameter of 2.0 to 10.0 nm, and wherein the polymer supported reagent is used for a reduction reaction of an aromatic nitro compound.

2. The polymer supported reagent in accordance with claim 1, wherein the mesoporous crosslinked polymer further comprises at least one polymer repeating unit selected from the group consisting of a styrene repeating unit and a vinyl repeating unit.

3. The polymer supported reagent in accordance with claim 1, wherein the polymer supported reagent has a shape of a spherical particle having a particle size of 20 to 300 μm.

4. The polymer supported reagent in accordance with claim 1, wherein the mesoporous crosslinked polymer comprises the repeating unit of Chemical Formula 1 and a styrene repeating unit at a mole ratio of 10:0 to 1:9.

5. A method of producing a polymer supported reagent comprising an acrylamide mesoporous crosslinked polymer including at least one repeating unit of Chemical Formula 1, which comprises the step of subjecting a monomer composition including an acrylamide monomer of Chemical Formula 2 to a suspension polymerization in the presence of a crosslinker and a radical initiator, wherein the polymer supported reagent comprises a plurality of pores having a diameter of 2.0 to 10.0 nm, wherein the monomer has a form of monoclinic monocrystal, and the crosslinker is selected from the group consisting of divinyl benzene, ethylene glycol di(meth)acrylate, buthylene glycol di(meth)acrylate, hexylene glycol di(meth)acrylate, methylene bisacrylamide, ethylene bisacrylamide, propylene bisacrylamide, ethylene glycol glycidyl ether, and polyethylene glycol glycidyl ether:

[Chemical Formula 1]

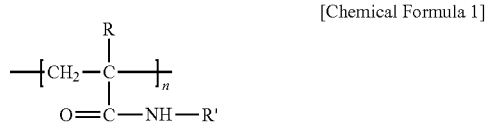

[Chemical Formula 2]

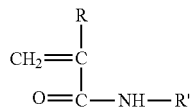

in Chemical Formula 1 and Chemical Formula 2,
n is an integer of 15 to 1800,
R is hydrogen or methyl,

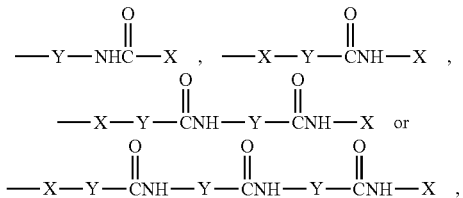

X is —Z-R",
Y is an alkylene of C1 to C10,
Z is an arylene of C6 to C20, and
R" is a linear or branched hydrocarbon of C10 to C20, or a linear or branched perfluorohydrocarbon of C10 to C20.

6. The method of producing a polymer supported reagent of claim 5, wherein the monomer composition further comprises at least one monomer selected from the group consisting of a styrene monomer and a vinyl monomer.

7. A method of producing a polymer supported reagent of claim 5, wherein the step of the suspension polymerization comprises the steps of dissolving the crosslinker, the radical initiator, and the monomer composition in an oil-soluble organic solvent to form an oil-soluble solution; and dispersing the oil-soluble solution in water with a surfactant dissolved therein to carry out the suspension polymerization.

8. The method of producing a polymer supported reagent of claim 5, wherein the radical initiator is selected from the group consisting of azobisisobutyronitrile (AIBN), benzoyl peroxide (BPO), and di-t-butyl peroxide (DTBP).

9. The method of producing a polymer supported reagent of claim 7, wherein the oil-soluble organic solvent comprises at least one selected from the group consisting of benzene, toluene, xylene, cyclohexene, n-pentane, and n-hexane.

10. The method of producing a polymer supported reagent of claim 7, wherein the surfactant comprises at least one selected from the group consisting of polyvinyl alcohol, hydroxypropyl methyl cellulose, polyethyleneglycol alkyl ether, polyoxyethylene octyl phenyl ether, polyoxyethylene sorbitol oleate, polyoxyethylene sorbitan monolaurate, polyoxyethylene sorbitan monostearate, polyoxyethylene sorbitan monoleate, sorbitan monolaurate, and sodium dodecyl benzene sulfonate.

11. The method of producing a polymer supported reagent of claim 5, wherein the suspension polymerization is carried out at a temperature of 40 to 90° C. for 4 to 12 hours.

12. A method of reducing an aromatic nitro compound, which comprises the step of subjecting an aromatic nitro compound to a reduction reaction in the presence of a polymer supported reagent comprising an acrylamide mesoporous crosslinked polymer including at least one repeating unit of Chemical Formula 1 and a reducing catalyst,
wherein the polymer supported reagent comprises a plurality of pores having a diameter of 2.0 to 10.0 nm:

[Chemical Formula 1]

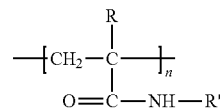

in Chemical Formula 1,
n is an integer of 15 to 1800,
R is hydrogen or methyl,
R' is X,

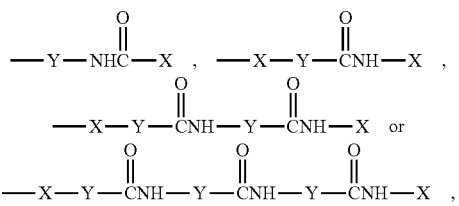

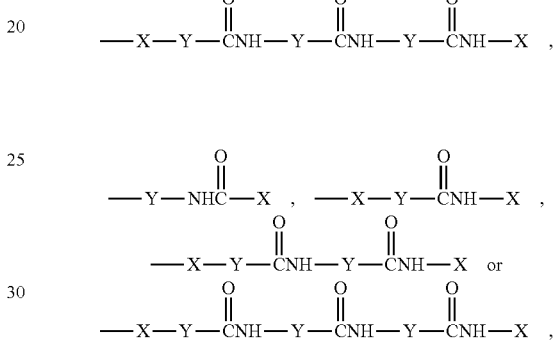

X is —Z-R",
Y is an alkylene of C1 to C10,
Z is an arylene of C6 to C20, and
R" is a linear or branched hydrocarbon of C10 to C20, or a linear or branched perfluorohydrocarbon of C10 to C20.

13. The method of reducing an aromatic nitro compound of claim 12, wherein the step of the reduction reaction comprises the steps of swelling the polymer supported reagent with a liquid aromatic nitro compound or an organic solution of an aromatic nitro compound; and subjecting the aromatic nitro compound to a reduction reaction in the presence of a reducing catalyst in water.

14. The method of reducing an aromatic nitro compound of claim 12, wherein the aromatic nitro compound is selected from the group consisting of nitrobenzene, o-methyl nitrobenzene, o-ethyl nitrobenzene, p-halogen nitrobenzene, p-methoxy nitrobenzene, 2,5-difluoronitrobenzene, methyl-2-nitrobenzoate, 3-nitrostyrene, and 1,3-dimethyl-2-nitrobenzene.

15. A method of reducing an aromatic nitro compound of claim 12, further comprising the step of extracting a reduction product from the polymer supported reagent after the step of the reduction reaction.

16. The method of reducing an aromatic nitro compound of claim 12, wherein the reduction reaction produces at least one reduction product selected from the group consisting of an aromatic azoxy compound, an aromatic azo compound, and an aromatic hydrazo compound.

17. The method of reducing an aromatic nitro compound of claim 12, wherein the reducing catalyst is selected from the group consisting of Zn, Cu, Ag, Au, Cd, Hg, Fe, $K_4[Fe(CN)_6]$, and $NaBH_4$.

18. The method of reducing an aromatic nitro compound of claim 17, wherein the reducing catalyst further comprises at least one cocatalyst selected from the group consisting of $NH_4Cl$, $H_2CO_3$, $H_3PO_4$, and a diluted HCl.

19. The method of reducing an aromatic nitro compound of claim 12, wherein the reduction reaction is carried out at a temperature of 50 to 90° C. for 2 to 48 hours.

* * * * *